(12) United States Patent
Adjouadi et al.

(10) Patent No.: US 11,989,932 B1
(45) Date of Patent: May 21, 2024

(54) SYSTEMS AND METHODS FOR COLOR-CODED VISUALIZATION TO AID IN DIAGNOSIS AND PROGNOSIS OF ALZHEIMER'S DISEASE

(71) Applicants: Malek Adjouadi, Miami, FL (US); Mohammad Eslami, Miami, FL (US); Solale Tabarestani, Miami, FL (US)

(72) Inventors: Malek Adjouadi, Miami, FL (US); Mohammad Eslami, Miami, FL (US); Solale Tabarestani, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/512,559

(22) Filed: Nov. 17, 2023

(51) Int. Cl.
  *G06T 7/00* (2017.01)
  *A61B 5/00* (2006.01)
  (Continued)

(52) U.S. Cl.
  CPC .......... *G06V 10/811* (2022.01); *A61B 5/4088* (2013.01); *G06T 7/0016* (2013.01); *G06T 11/001* (2013.01); *G06V 10/7715* (2022.01); *G16H 50/20* (2018.01); *G06T 2207/10024* (2013.01); *G06T 2207/10088* (2013.01); *G06T 2207/10104* (2013.01); *G06T 2207/30016* (2013.01); *G06T 2207/30204* (2013.01); *G06V 2201/03* (2022.01)

(58) Field of Classification Search
  CPC . G06T 2207/30204; G06T 2207/30016; G06T 2207/10104; G06T 2207/10088; G06T 2207/10024; G06T 7/0016; G06T 11/001; G06T 2207/10081; G06T 2207/30096; G06T 2207/20221; G06T 2207/20084; G06T 7/0012; G06V 10/811; G06V 10/7715; G06V 2201/03; G16H 50/20; G16H 50/70; G16H 50/30; A61B 5/4088; A61B 6/501; A61B 6/5217; A61B 5/383; A61B 5/4064; A61B 5/377; A61B 5/374; G16Z 99/00

See application file for complete search history.

(56) References Cited

U.S. PATENT DOCUMENTS

| | | | | |
|---|---|---|---|---|
| 2002/0187502 | A1* | 12/2002 | Waterman | C07K 14/4705 435/6.14 |
| 2012/0296569 | A1* | 11/2012 | Shahaf | A61B 5/383 702/19 |
| 2023/0414189 | A1* | 12/2023 | Saeed | A61B 6/5235 |

OTHER PUBLICATIONS

Amini et al., "Multi-level multi-modality (PET and CT) fusion radiomics: Prognostic-modeling for non-small cell lung carcinoma", Physics in medecine & biology, 2021, vol. 66(20), p. 205017; England:IOP Publishing. (Year: 2021).*

* cited by examiner

*Primary Examiner* — Wesner Sajous
(74) *Attorney, Agent, or Firm* — Saliwanchik, Lloyd & Eisenschenk

(57) ABSTRACT

Systems and methods are provided for color-coded visualization to aid in diagnosis and prognosis of Alzheimer's disease (AD). The color-coded visualization mechanism can be driven by an integrated machine learning (ML) model, which can take as its inputs neuroimaging (e.g., magnetic resonance imaging (MRI), positron emission tomography (PET)) data, neuropsychological test scores, the cerebrospinal fluid (CSF) biomarker, and/or risk factors. With these inputs, the ML model can generate a color-coded visualization of the disease state.

18 Claims, 20 Drawing Sheets

(51) Int. Cl.
*G06T 11/00* (2006.01)
*G06V 10/77* (2022.01)
*G06V 10/80* (2022.01)
*G16H 50/20* (2018.01)

Study population and subgroups.

| Categories based on diagnosis | | | | | Categories based on conversion | | | | |
|---|---|---|---|---|---|---|---|---|---|
| Number of samples # | | | Total | | | | # | Description | |
| | CN | AD | MCI | | | CN | 329 | Stable Normal | |
| Baseline | 331 | 163 | 629 | 1123 | Impaired | Others | 8 | Others (e.g. MCI to CN) | |
| 6th month | 331 | 195 | 597 | 1123 | | AD | 163 | Stable Dementia | |
| 12th month | 332 | 243 | 548 | 1123 | | MCI | 442 | Stable MCI | |
| 24th month | 334 | 342 | 447 | 1123 | | MCIc | 181 | MCI converter to AD | |
| | | | | | | | 786 | Total Impaired | |
| | | | | | | | 1123 | Total | |

FIG. 6

ADNI (QT-pad challenge) dataset with the features extracted from each modality/source at baseline.

Number of subjects: 1123

| Modality | Feature | Minimum Value | Average Value | Maximum Value | Number of missed values at baseline |
|---|---|---|---|---|---|
| MRI | Ventricular volume | 5650.0 | 39,420.220 | 145,115.0 | 99 |
| | Hippocampus volume | 3091.0 | 6798.67 | 10,769.0 | 158 |
| | Whole Brain volume | 736,813.0 | 1,022,118.21 | 1,443,990.50 | 10 |
| | Entorhinal Cortical thickness | 1426.0 | 3507.23 | 5896.0 | 160 |
| | Fusiform | 8991.0 | 17,354.76 | 26,280.0 | 160 |
| | Middle temporal gyrus | 9275.0 | 19,545.76 | 29,435.0 | 160 |
| | Intracranial volume (ICV) | 1,116,279.11 | 1,536,383.48 | 2,073,473.30 | 0 |
| PET | 'FDG' | 0.69 | 1.24 | 1.707169 | 321 |
| | Pittsburgh Compound-B (PIB) | 1.10 | 1.53 | 1.89 | 1116 |
| | 'AV45' | 0.85 | 1.19 | 2.02 | 614 |
| Cognitive Test | RAVLT immediate | 7.0 | 35.59 | 71.0 | 3 |
| | RAVLT learning | -2.0 | 4.29 | 11.0 | 3 |
| | RAVLT forgetting | -5 | 4.35 | 13.0 | 3 |
| | RAVLT percforgetting | -100.0 | 57.37 | 100.0 | 4 |
| | Functional Activities Questionnaires (FAQ) | 0.0 | 3.73 | 30.0 | 4 |
| | Montreal Cognitive Assessment (MoCA) | 10.0 | 23.78 | 30.0 | 616 |
| | Everyday Cognition (Ecog): 'EcogPtMem' | 1.0 | 2.12 | 4.0 | 613 |
| | Ecog: 'EcogPtLang' | 1.0 | 1.73 | 4.0 | 612 |
| | Ecog: 'EcogPtVispat' | 1.0 | 1.37 | 4.0 | 614 |
| | Ecog: 'EcogPtPlan' | 1.0 | 1.49 | 4.0 | 612 |
| | Ecog: 'EcogPtOrgan' | 1.0 | 1.48 | 4.0 | 624 |
| | Ecog: 'EcogPtDivatt' | 1.0 | 1.79 | 4.0 | 615 |
| | Ecog: 'EcogPtTotal' | 1.0 | 1.67 | 3.52 | 612 |
| | Ecog: 'EcogSPMem' | 1.0 | 2.01 | 4.0 | 615 |
| | Ecog: 'EcogSPLang' | 1.0 | 1.56 | 4.0 | 614 |
| | Ecog: 'EcogSPVispat' | 1.0 | 1.38 | 4.0 | 622 |
| | Ecog: 'EcogSPPlan' | 1.0 | 1.50 | 4.0 | 616 |
| | Ecog: 'EcogSPOrgan' | 1.0 | 1.57 | 4.0 | 628 |
| | Ecog: 'EcogSPDivatt' | 1.0 | 1.78 | 4.0 | 621 |
| | Ecog: 'EcogSPTotal' | 1.0 | | 3.89 | 614 |
| CSF | Amyloid Beta (ABETA) | 300.0 | 984.94 | 1700.0* | 335 |
| | phosphorylated tau protein (PTAU) | 0 | 27.45 | 94.86 | 335 |
| | Total tau protein (TAU) | 80 | 284.98 | 816.0 | 335 |
| Risk factors | Age | 55.0 | 73.93 | 91.4 | 0 |
| | years of education | 6.0 | 15.92 | 20 | 0 |
| | APOE4 | 0 | 0.56 | 2 | 0 |
| | Gender | | | | 0 |

FIG. 7

Processing time of machine learning model.

| Image size (pixels) | Trainable parameters | Train time (s) | Test time per subject (s) |
|---|---|---|---|
| 23 × 23 | 36,143 | 4000 epochs: 275.67 | 0.008 |
| 45 × 45 | 126,443 | 4000 epochs: 987.94 | 0.017 |

FIG. 8

Classification outcomes as assessed by three raters.

| Classification type | Correctly classified | Misclassified outcomes | Inconclusive outcomes |
|---|---|---|---|
| 3-Way (CN, impaired, others) | 0.82 ± 0.03 | 0.15 ± 0.004 | 0.023 ± 0.002 |
| 5-way (CN, MCI, MCIc, AD, others) | 0.68 ± 0.05 | 0.29 ± 0.01 | 0.023 ± 0.002 |

FIG. 9

GM/WM regions considered

1) LH_CAUDALANTERIORCINGULATE
2) LH_CAUDALMIDDLEFRONTAL
3) LH_CUNEUS
4) LH_ENTORHINAL
5) LH_FRONTALPOLE
6) LH_FUSIFORM
7) LH_INFERIORPARIETAL
8) LH_INFERIORTEMPORAL
9) LH_INSULA
10) LH_ISTHMUSCINGULATE
11) LH_LATERALOCCIPITAL
12) LH_LATERALORBITOFRONTAL
13) LH_LINGUAL
14) LH_MEDIALORBITOFRONTAL
15) LH_MIDDLETEMPORAL
16) LH_PARACENTRAL
17) LH_PARAHIPPOCAMPAL
18) LH_PARSOPERCULARIS
19) LH_PARSORBITALIS
20) LH_PARSTRIANGULARIS
21) LH_PERICALCARINE
22) LH_POSTCENTRAL
23) LH_POSTERIORCINGULATE

24) LH_PRECENTRAL
25) LH_PRECUNEUS
26) LH_ROSTRALANTERIORCINGULATE
27) LH_ROSTRALMIDDLEFRONTAL
28) LH_SUPERIORFRONTAL
29) LH_SUPERIORPARIETAL
30) LH_SUPERIORTEMPORAL
31) LH_SUPRAMARGINAL
32) LH_TEMPORALPOLE
33) LH_TRANSVERSETEMPORAL
34) LH_BANKSSTS
35) RH_CAUDALANTERIORCINGULATE
36) RH_CAUDALMIDDLEFRONTAL
37) RH_CUNEUS
38) RH_ENTORHINAL
39) RH_FRONTALPOLE
40) RH_FUSIFORM
41) RH_INFERIORPARIETAL
42) RH_INFERIORTEMPORAL
43) RH_INSULA
44) RH_ISTHMUSCINGULATE
45) RH_LATERALOCCIPITAL
46) RH_LATERALORBITOFRONTAL

47) RH_LINGUAL
48) RH_MEDIALORBITOFRONTAL
49) RH_MIDDLETEMPORAL
50) RH_PARACENTRAL
51) RH_PARAHIPPOCAMPAL
52) RH_PARSOPERCULARIS
53) RH_PARSORBITALIS
54) RH_PARSTRIANGULARIS
55) RH_PERICALCARINE
56) RH_POSTCENTRAL
57) RH_POSTERIORCINGULATE
58) RH_PRECENTRAL
59) RH_PRECUNEUS
60) RH_ROSTRALANTERIORCINGULATE
61) RH_ROSTRALMIDDLEFRONTAL
62) RH_SUPERIORFRONTAL
63) RH_SUPERIORPARIETAL
64) RH_SUPERIORTEMPORAL
65) RH_SUPRAMARGINAL
66) RH_TEMPORALPOLE
67) RH_TRANSVERSETEMPORAL

FIG. 10

SYSTEMS AND METHODS FOR COLOR-CODED VISUALIZATION TO AID IN DIAGNOSIS AND PROGNOSIS OF ALZHEIMER'S DISEASE

GOVERNMENT SUPPORT

This invention was made with government support under CNS1920182 awarded by the National Science Foundation. The government has certain rights in the invention.

BACKGROUND

Challenges persist in multiclass classification of the different stages of Alzheimer's disease (AD) and in the prediction of the trajectory of decline to determine whether a given patient is benefiting from a treatment or from a prescribed medication over time.

BRIEF SUMMARY

Embodiments of the subject invention provide novel and advantageous systems and methods for color-coded visualization to aid in diagnosis and prognosis of Alzheimer's disease (AD). The challenges that persist in multiclass classification of the different stages of AD and in the prediction of the trajectory of decline are mainly due to the variability of data and the lack of ability to handle the challenges of missing data and multicollinearity inherent in longitudinal studies. Embodiments of the subject invention augment the deliberation process when analyzing medical data to ensure enhanced diagnosis, prognosis, and decision making through machine learning and novel color-coded visualization mechanisms. The machine learning-based color-coded visualization, which can be referred to herein as Machine Learning for Visualization (ML4Vis), provides a unique design approach to yield images that express visually disease progression to augment and facilitate the diagnosis and prognosis of AD (e.g., in longitudinal studies and/or cross-sectional studies). The novel color-coded visualization mechanism is driven by an integrated machine learning (ML) model, which can take as its inputs neuroimaging (e.g., magnetic resonance imaging (MRI), positron emission tomography (PET)) data, neuropsychological testing (or test scores), the cerebrospinal fluid (CSF) biomarker (as means to gauge levels of Amyloid Beta (ABETA), phosphorylated tau protein (PTAU), and/or total tau protein (TAU)), and/or risk factors (e.g., age, gender, years of education, and/or ApoE4 biomarker as one of the main variants of the apolipoprotein E (ApoE) gene). With these inputs, the ML model can generate a color-coded visualization of the disease state (e.g., in cross-sectional studies) and of disease progression (e.g., in longitudinal studies).

In an embodiment, a system for color-coded visualization to aid in diagnosis and prognosis of AD can comprise: a processor; and a machine-readable medium in operable communication with the processor and having instructions stored thereon that, when executed by the processor, perform the following steps: a) receiving multimodal input data about a subject, the multimodal input data comprising neuroimaging data of the subject; b) utilizing an ML model on the multimodal input data to perform intra-modality feature extraction and inter-modality feature extraction, followed by multimodal fusion to give fused data; and c) utilizing the ML model to perform tensorization on the fused data to generate a visual output image, the visual output image being color-coded based on a prognosis of AD for the subject. The neuroimaging data can comprise MRI data of the subject and/or PET data of the subject. The multimodal input data can further comprise CSF biomarker data of the subject (e.g., as means to gauge levels of ABETA, PTAU, and/or TAU), cognitive task result data of the subject, and/or risk factor data of the subject (e.g., age, gender, years of education, and/or ApoE4 biomarker as one of the main variants of the apolipoprotein E (ApoE) gene). The ML model can comprise: a first part comprising a first plurality of layers configured to perform the intra-modality feature extraction, the inter-modality feature extraction, and the multimodal fusion; and a second part comprising a second plurality of layers configured to perform the tensorization on the fused data to generate the visual output image. The second part can be further configured to perform: extra feature extraction on the fused data; and/or drop-out and batch normalization on the fused data. The first plurality of layers can comprise at least five layers (e.g., exactly five layers), and/or the second plurality of layers can comprise at least five layers (e.g., exactly five layers). The visual output image can be color-coded such that: a first color (e.g., green) represents cognitively normal (CN); a second color (e.g., blue) different from the first color represents mild cognitive impairment (MCI); a third color (e.g., red) different from the first color and the second color represents AD; the visual output image comprises a bar representing a region of uncertainty (RU), the bar being a fourth color (e.g., black) that is different from the first color, the second color, and the third color, a fifth color (e.g., yellow, cyan, or magenta) different from the first color, the second color, the third color, and the fourth color represents early MCI (EMCI); and/or a sixth color (e.g., yellow cyan, or magenta) different from the first color, the second color, the third color, the fourth color, and the fifth color represents late MCI (LMCI). The system can further comprise a display in operable communication with the processor and/or the machine-readable medium and configured to display the visual output image, diagnosis information for the subject, and/or prognosis information for the subject. The image can be, for example, at least 23×23 pixels (e.g., 45×45 pixels). The subject can be, for example, a human subject.

In another embodiment, a method for color-coded visualization to aid in diagnosis and prognosis of AD can comprise: a) receiving (e.g., by a processor) multimodal input data about a subject, the multimodal input data comprising neuroimaging data of the subject; b) utilizing (e.g., by the processor) an ML model on the multimodal input data to perform intra-modality feature extraction and inter-modality feature extraction, followed by multimodal fusion to give fused data; and c) utilizing (e.g., by the processor) the ML model to perform tensorization on the fused data to generate a visual output image, the visual output image being color-coded based on a prognosis of AD for the subject. The neuroimaging data can comprise MRI data of the subject and/or PET data of the subject. The multimodal input data can further comprise CSF biomarker data of the subject (e.g., as means to gauge levels of ABETA, PTAU, and/or TAU), cognitive task result data of the subject, and/or risk factor data of the subject (e.g., age, gender, years of education, and/or ApoE4 biomarker as one of the main variants of the ApoE gene). The ML model can comprise: a first part comprising a first plurality of layers configured to perform the intra-modality feature extraction, the inter-modality feature extraction, and the multimodal fusion; and a second part comprising a second plurality of layers configured to perform the tensorization on the fused data to generate the visual output image. The second part can be further configured to perform: extra feature extraction on the fused data; and/or drop-out and batch normalization on the fused data. Step c) can further comprise performing extra feature extraction on the fused data and/or drop-out and batch normalization on the fused data to generate the visual output image. The first plurality of layers can comprise at least five layers (e.g., exactly five layers), and/or the second plurality of layers can comprise at least five layers (e.g., exactly five layers). The visual output image can be color-coded such that: a first color (e.g., green) represents CN; a second color (e.g., blue) different from the first color represents MCI; a third color (e.g., red) different from the first color and the second color represents AD; the visual output image comprises a bar representing an RU, the bar being a fourth color (e.g., black) that is different from the first color, the second color, and the third color, a fifth color (e.g., yellow, cyan, or magenta) different from the first color, the second color, the third color, and the fourth color represents EMCI; and/or a sixth color (e.g., yellow cyan, or magenta) different from the first color, the second color, the third color, the fourth color, and the fifth color represents LMCI. The method can further comprise displaying (e.g., on a display in operable communication with the processor) the visual output image, diagnosis information for the subject, and/or prognosis information for the subject. The method can further comprise providing the diagnosis and/or prognosis to the subject and/or to a health care provider to aid in a care plan and/or a treatment plan (e.g., a treatment plan for AD or a care plan to minimize chances of developing AD). The image can be, for example, at least 23×23 pixels (e.g., 45×45 pixels). The subject can be, for example, a human subject.

BRIEF DESCRIPTION OF DRAWINGS

FIG. 1(a) shows stable cognitively normal (CN); FIG. 1(b) shows stable mild cognitive impaired (MCI); FIG. 1(c) shows stable Alzheimer's disease (AD); FIG. 1(d) shows CN converting to MCI at the 24th month (T24); FIG. 1(e) shows MCI that progressed to AD at the 6th month (T6); FIG. 1(f) shows MCI that progressed to AD at the 12th month (T12); and FIG. 1(g) shows MCI that progressed to AD at T24. In each image, the dark black vertical bar represents a region of uncertainty (RU).

FIGS. 3(a)-3(w) show visualizations of AD. In each of FIGS. 3(a)-3(w), the two images to the lower left of the figure show a target visual output for a test subject (left-most image) and a machine learning (ML) visual output for the test subject (right-most image of the two images located at the lower left of the figure). FIGS. 3(a)-3(d) show cases for four different stable CN subjects, respectively. FIGS. 3(q)-3(t) show cases for four different stable AD subjects, respectively.

FIGS. 3(u)-3(w) show cases for three different challenging stable subjects, respectively, where the ML outcome is different from the target. The Alzheimer's Disease Neuroimaging Initiative (ADNI) dataset was used as data for FIGS. 3(a)-3(w) (see also adni.loni.usc.edu, which is hereby incorporated herein by reference in its entirety). The ADNI patient/record identification numbers (RIDs) for the subjects for FIGS. 3(a)-3(w) are: FIG. 3(a), 4491; FIG. 3(b), 4376; FIG. 3(c), 4422; FIG. 3(d), 4421; FIG. 3(e), 4531; FIG. 3(f), 2068; FIG. 3(g), 4871; FIG. 3(h), 4346; FIG. 3(i), 4277; FIG. 3(j), 4813 FIG. 3(k), 2047 FIG. 3(l), 4426; FIG. 3(m), 4595; FIG. 3(n), 4167; FIG. 3(o), 4542; FIG. 3(p), 4189; FIG. 3(q), 4252; FIG. 3(r), 4338; FIG. 3(s), 4494; FIG. 3(t), 4001; FIG. 3(u), 4226; FIG. 3(v), 4339; and FIG. 3(w), 4676.

FIGS. 4(a)-4(d) show a target image, an ML visual outcome image, an ML blue channel image, and an ML red channel image, respectively. FIGS. 4(e) and 4(f) show the L component of FIG. 4(a) and the L component of FIG. 4(b), respectively. FIGS. 4(g) and 4(h) show a 3D display of FIG. 4(c) and a 3D display of FIG. 4(d), respectively.

FIG. 6 shows a table of a study population and subgroups.
FIG. 7 shows a table of the ADNI dataset with features extracted from each modality/source at baseline.
FIG. 8 shows a table of processing time of an ML model.
FIG. 9 shows a table of classification outcomes as assessed by three raters.
FIG. 10 shows a table of brain regions for the standard uptake value ratios (SUVRs) in FIGS. 3(a)-3(w).

DETAILED DESCRIPTION

Figures 1A, 1B, 1C, 1D, 1E, 1F, 1G:
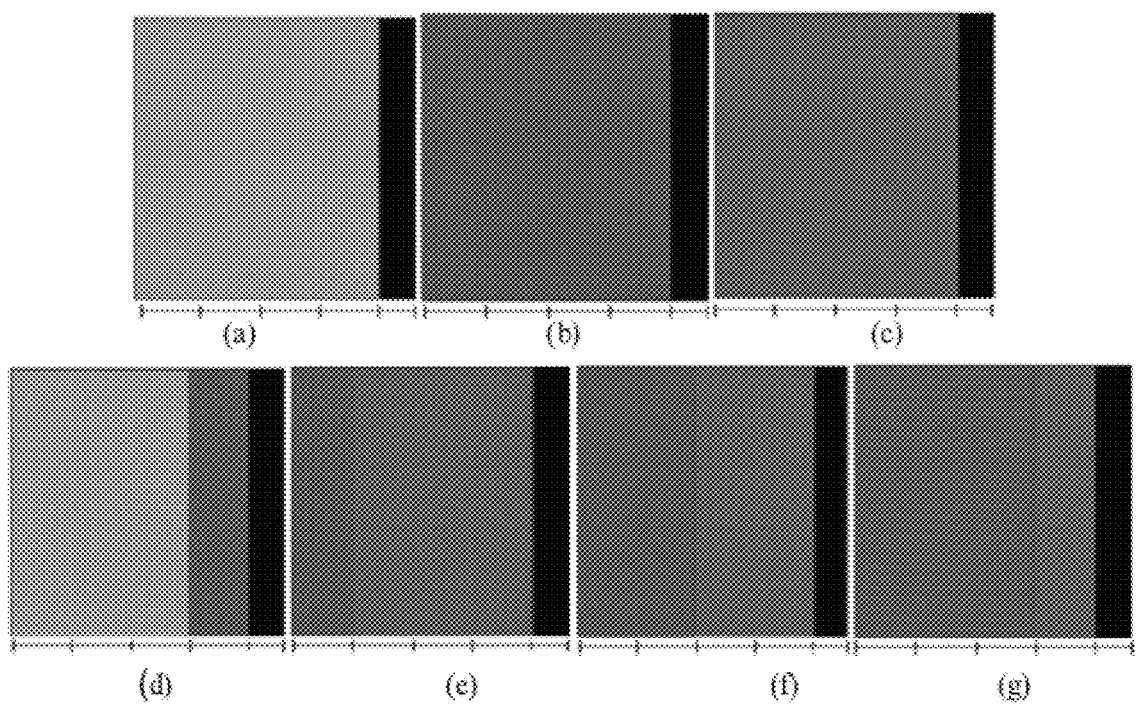
FIGS. 1(a)-1(g) show designed target images for different states, which can be generated according to embodiments of the subject invention.

Embodiments of the subject invention provide novel and advantageous systems and methods for color-coded visualization to aid in diagnosis and prognosis of Alzheimer's disease (AD). Embodiments augment the deliberation process when analyzing medical data to ensure enhanced diagnosis, prognosis, and decision making through machine learning and novel color-coded visualization mechanisms. The machine learning-based color-coded visualization, which can be referred to herein as Machine Learning for Visualization (ML4Vis), provides a unique design approach to yield images that express visually disease progression to augment and facilitate the diagnosis and prognosis of AD (e.g., in longitudinal studies and/or cross sectional studies). The novel color-coded visualization mechanism can be driven by an integrated machine learning (ML) model, which can take as its inputs neuroimaging (e.g., magnetic resonance imaging (MRI), positron emission tomography (PET)) data, neuropsychological testing (or test scores), the cerebrospinal fluid (CSF) biomarker (as means to gauge levels of Amyloid Beta (ABETA), phosphorylated tau protein (PTAU), and/or total tau protein (TAU)), and/or risk factors (e.g., age, gender, years of education, and/or ApoE4 biomarker as one of the main variants of the apolipoprotein E (ApoE) gene). With these inputs, the ML model can generate a color-coded visualization of the disease state (e.g., in cross-sectional studies) and of disease progression (e.g., in longitudinal studies).

Embodiments of the subject invention provide at least the following advantageous features: (1) a more realistic way to visualize disease state and progression in time; (2) augmenting prospects for more enhanced diagnosis and prognosis of the disease; (3) a continuum of outcomes that may define the earliest stages of the disease to allow for early treatment and therapeutic intervention; (4) an understanding of the interplay between multimodal features and measurements, together with the complex choreography they engender, which now can be ascertained more intuitively through the visualization model; (5) ability to ascertain relevance of features through visualization with and without them used as input features to the machine learning process, hence augmenting the understanding of the causal effects they have in the different transition phases of the disease, and in deciphering the intricacies of data in terms of variability, interrelatedness, and influence in time of these features on cognition, structure, and function; and (6) because contextual information is added, the machine learning generated visual outcome can be compared to the target image as defined at baseline cross-sectionally or at the different time points of a longitudinal study to see if assigned cognitive scores (e.g., mini-mental state examination (MMSE) and/or clinical dementia rating (CDR) scale) and other extracted features (e.g., standardized uptake value ratio (SUVR)) from PET coincide more with the target image or with the machine learning generated image for validation and deliberation purposes.

The advantage of an image (compared to text only), together with the challenge imposed by the variability of the multimodal features, served as an incentive to create the ML4Vis of AD, which can also be referred to herein as the ML4VisAD model. The color image can use the standard color space (e.g., red, green, blue (RGB)) and can have any suitable size (e.g., 23×23×3). The color image can serve as an output image with quantifiable uncertainty (which can be represented by a black bar) to be contrasted with the ideal outcome represented by the target image. Given the nature of the color-coded output image, with the many variants of the images generated via machine learning, it can be understood why multiclass classification is challenging in terms of attaining high accuracy, and why labeling a particular subject through neuropsychological testing at baseline is not that evident. Clinician and AD experts often disagree and deliberate for a long time before reaching a certain decision on a label to be associated with a given subject, such as cognitively normal (CN), mild cognitive impairment (MCI), and AD as the last prodromal stage. ML4VisAD can serve as a more intuitive way for visualizing disease progression as well as for assessing the prediction of a given outcome.

ML4Vis can also reflect some uncertainty to facilitate deliberation and decision-making. Moreover, as the examples herein would indicate, the traditional labeling of CN, MCI, and AD, and even with the addition of early and late MCI groups (EMCI, LMCI) as subdivisions of the MCI group may not be sufficient to describe the many stages that can be reflected visually through machine learning. ML4VisAD can offer alternative ways to describe these slow and gradual changes of the disease through visualization with a quantifiable degree of uncertainty that is introduced by the machine learning process itself. The examples show the potential for use of the LM4VisAD model for brain research and for smart health in general.

The color-coded output image can have any suitable size (e.g., 23×23 or 45×45 pixels). A size of 23×23 size is still good enough for visual scrutiny and deliberation. Embodiments of the subject invention are amenable to using other tensor structures, having additional time points in longitudinal studies, having a single time point as in the case of cross-sectional studies, and adding more colors if additional labels are considered (e.g., EMCI and LMCI). In the case of adding more colors, as an example, RGB can be used together with other colors (e.g., yellow, cyan, and magenta (YCM)) to include other labels.

FIGS. 1(a)-1(g) show color-coded target images (each 23×23×3), each image including a region of uncertainty (RU) represented by the dark (black) bar. The RGB channels were used in FIGS. 1(a)-1(g) to represent the state of the disease with different colors (AD as red, MCI as blue, and CN as green). In this color-coded scheme, subjects that are stable over time would display a single color as in the cases for FIGS. 1(a) (CN), 1(b), (MCI), and 1(c) (AD). Subjects who convert at specific time points to other states would display two or more colors as in the cases in FIGS. 1(d) (CN to MCI), 1(e) (MCI to AD), 1(f) (MCI to AD), and 1(g) (MCI to AD). Cognitive status through a 24-month timeline (e.g., including baseline (T0) and referral sessions, such as three referral sessions (e.g., T6 (6th month), T12 (12th month), and T24 (24th month))) can be used define trajectories of the disease state. In order to assess the degree of uncertainty that the ML model may inject into the process, a black bar can be added as an RU (e.g., after the bar representing the T24 time point). This black bar could be situated anywhere in the display and is there solely to estimate the degree of uncertainty the ML model injects into the visual output through its many inner computations. A perfect ML model would leave the black bar unchanged (i.e., zero effect), meaning that the ML model is stable and has performed its task reliably. The size (e.g., 23×23) of the RGB image can be any N×N dimension, where N is an integer. A target image with a higher resolution (e.g., 45×45) can provide an output image that is more detailed and with smoother transition phases. However, the ML model may need more convolutional layers with a higher N, which would lead to more training/processing time.

Figure 2:
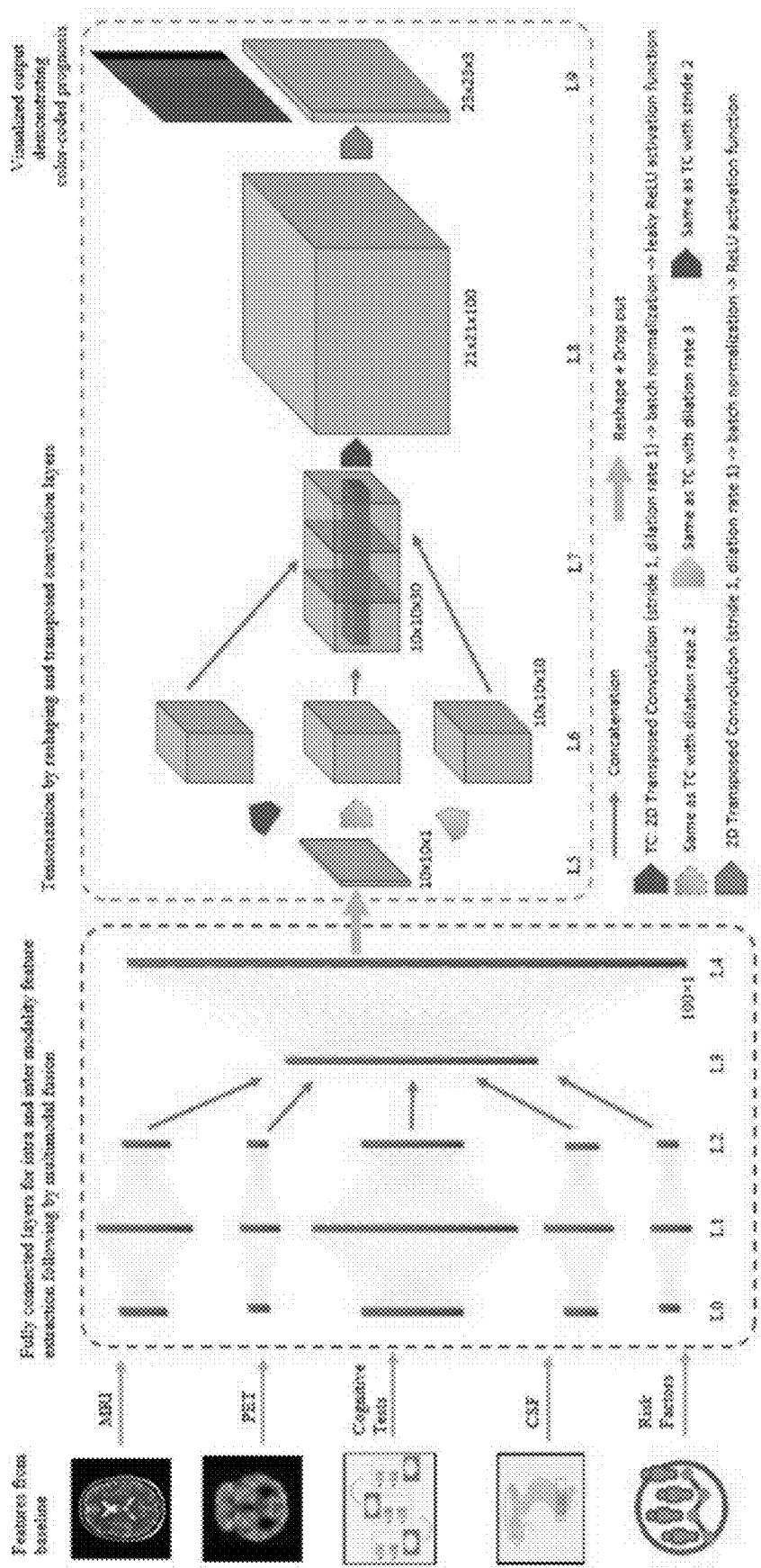
FIG. 2 shows a schematic view of an architecture of a color-coded visualization system, according to an embodiment of the subject invention.

FIG. 2 shows an architecture of a system for color-coded visualization to aid in diagnosis and prognosis of AD, according to an embodiment of the subject invention. Referring to FIG. 2, the overall objective was to model a network estimator E in which $I_{target}=E(x_1, x_2, x_3, x_4, x_5)$ is a colorful image similar to those shown in FIG. 1(a)-1(g), and where the input space is the multimodal features of $\{x_1, x_2, x_3, x_4, x_5\}$ in which each vector $x_m$ comprises the extracted measurements from modality m at baseline. Features extracted from MRI, PET, CSF, cognitive tasks, and the risk factors, as shown in the table in FIG. 7, can serve as input to the ML4VisAD model. The network can be designed to have two parts (p1, p2) such that the initial layers address the intra/inter-modality feature extraction via fully connected layers (p1,) and the second part involves tensorization, extra feature extraction, and image production (p2). Thus, $I_{predicted}=p2(p1(x_1, x_2, x_3, x_4, x_5))$ and the difference between $I_{predicted}$ and $I_{target}$ is optimized for each observation/patient.

With the fully connected layers, the network converts the basic features for each modality into a primary representation space. Layers L0, L1, and L2 are to transform the features extracted from input data (e.g., MRI, PET, CSF, neurocognitive measurements, and/or risk factors) into an initial feature space representation specific to each modality.

The size of the input node in layer L0 for each modality m is the length of the input feature vector $n_m=length(x_m)$, which then goes through two more fully connected layers, L1 and L2, with 2×n. and n. nodes, respectively, followed by linear activation layers. The previous fully connected layers of L2 are integrated into L3 by concatenating the outputs of the L2 layer to initiate the inter-modality feature space and create a new modality representation. Feature fusion and feature extraction are accomplished in the inter-modality phase using concatenation (L3) and a fully connected layer (L4).

Layers L5 to L9 are for tensorization due to two reasons: (1) because the input data format to the network includes vectors from different modalities, and the target output is a colorful image, the vectors need to be reshaped to matrices to generate colorful two-dimensional (2D) images; and 2) layers L0 to L4 were necessary to use information from the different modalities and model progression of the disease. However, combining the features from different modalities in a standard network may not consider the heterogeneity of the data. Using a non-linear mapping function to transform the feature space into a higher-dimensional receptive field can help the network identify more significant relationships.

The network architecture utilizes reshaping and convolutional neural layers for tensorization and extracting higher-order features from multimodal features. A tensor with dimensions of 10×10×30 can be generated using the following steps through layers L5, L6, and L7. Layer L5 reshapes the 100-node output vector of layer L4 to create a 2D tensor with dimensions of 10×10. Layer L6 conducts 2D transpose convolutional filtering with three different dilation rates 1, 2, and 3. For each dilation rate, there are ten kernels with 3×3 kernel size, the stride of 1, and padding of type same. Layer L7 is a concatenation of the three output tensors from layer L6. Layer L8 is also a 2D transpose convolution but with 100 kernels of size 3×3 and a stride of 2. Last, the L9 produces the output image $I_{predicted}$ by 2D transpose convolution with three kernels of size 3×3 and a stride of 1. Padding in layers L8 and L9 are of type valid, which does not include zero padding.

Drop-out and batch normalization can also be applied in layers L6, L8, and L9 to prevent or inhibit overfitting. Design details and tensor dimensions for the different layers are shown in FIG. 2 as well. A GitHub repository (see, github.com/mohaEs/ML4VisAD; which is hereby incorporated by reference in its entirety) provides the implementation codes.

A loss function that can be used is the mean absolute error (MAE) between the target image and the produced output (i.e., loss=MAE($I_{target}-I_{predicted}$)). A cross-validation over subjects can be used (e.g., a 10-fold cross-validation over subjects), and in each training session, a portion of the training set (e.g., less than 20%, such as 10% or about 10%) can be used as a validation set (i.e., ten times of training data split to 81/9/10% as train/validation/test). A larger number of epochs (e.g., 4000 epochs) with a predetermined batch size (e.g., batch size of 500) can be used to train the network. In order to produce a larger image size (e.g., 45×45 image size), one or more layers (e.g., the L8 layer) can be replicated.

Figures 3A, 3B:
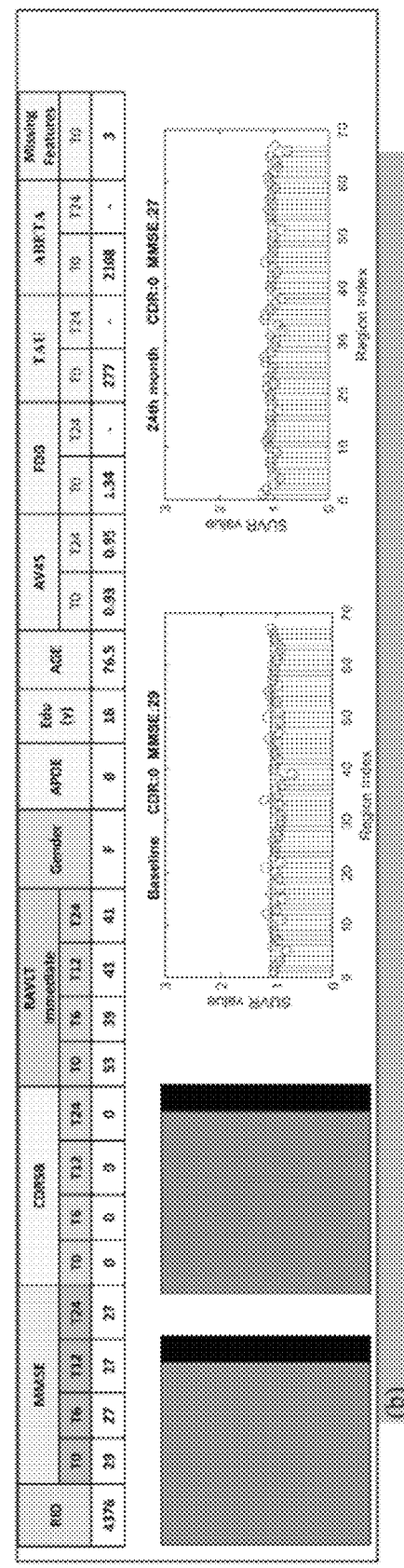
Figure 3C:
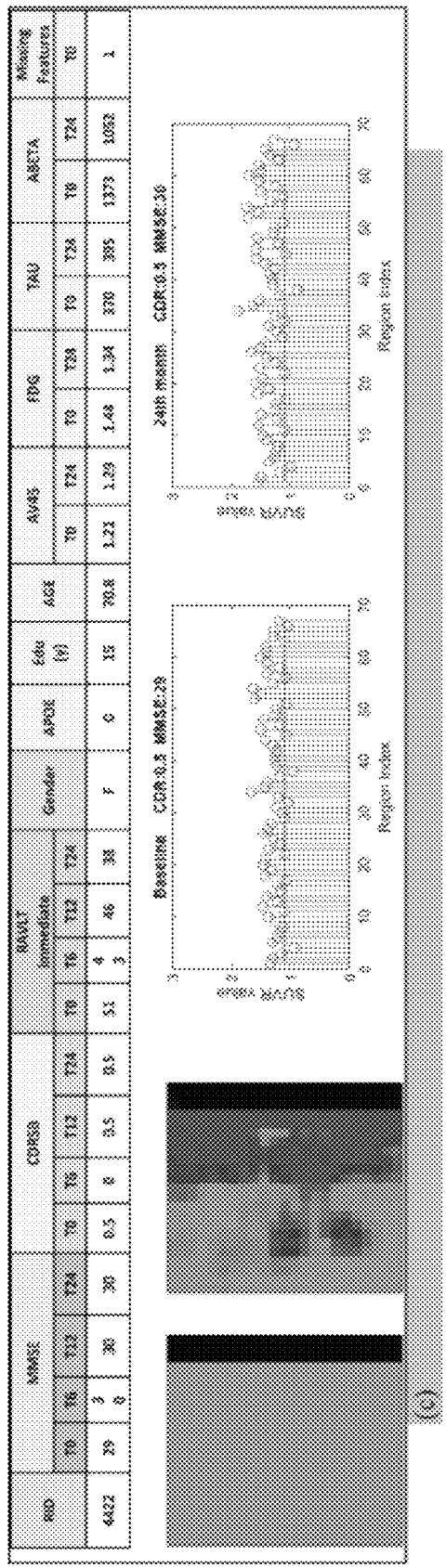
Figure 3D:
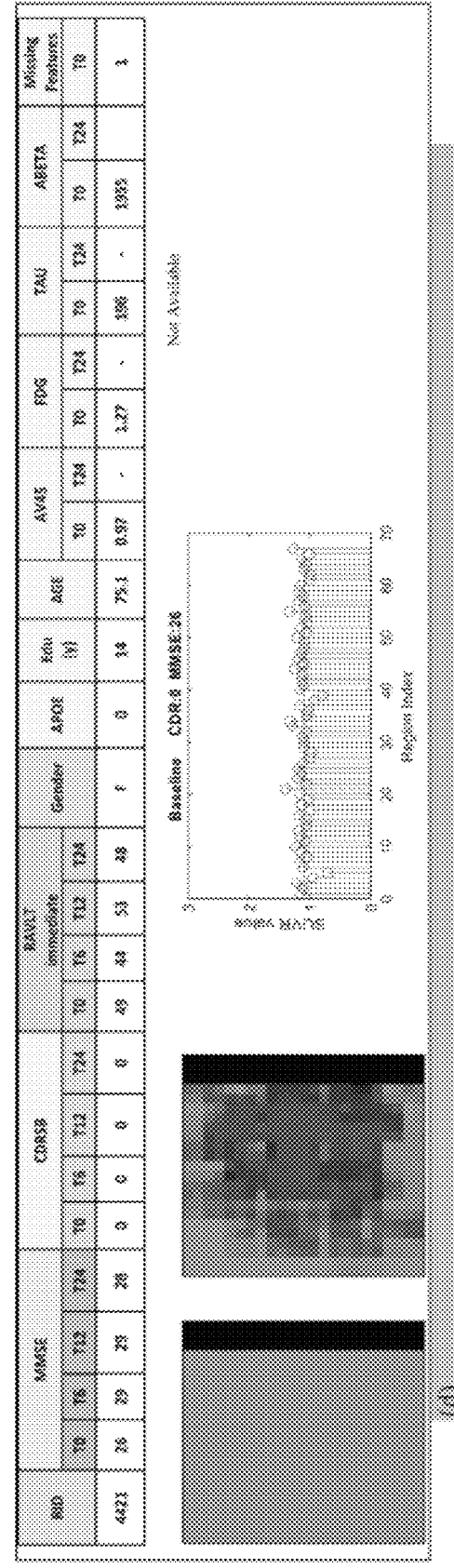
Figure 3E:
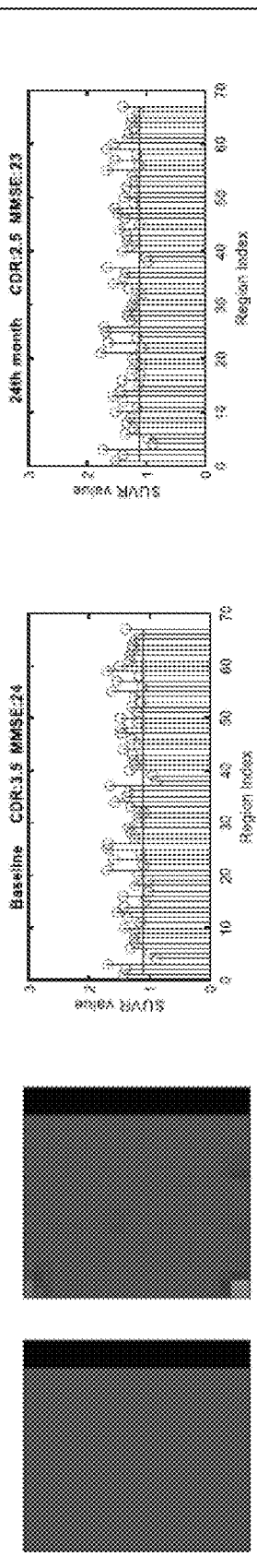
FIGS. 3(e)-3(h) show cases for four different stable MCI subjects, respectively.
Figure 3F:
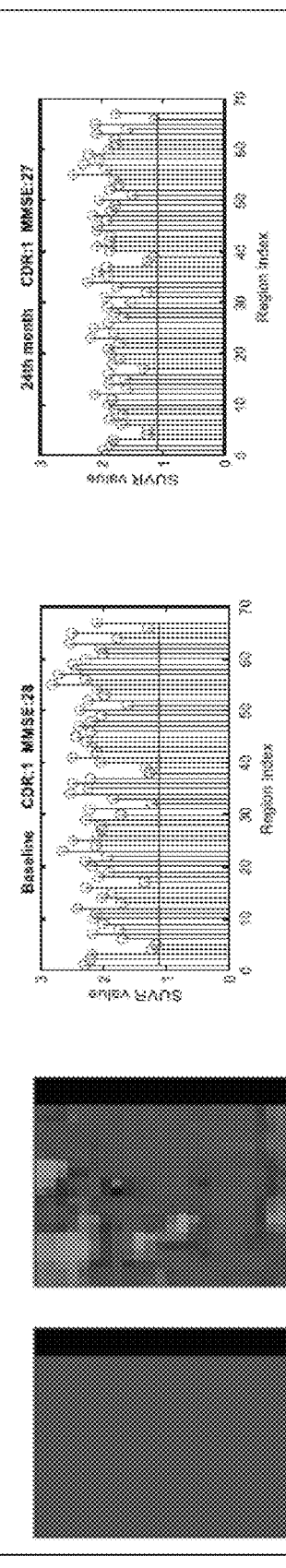
Figure 3G:
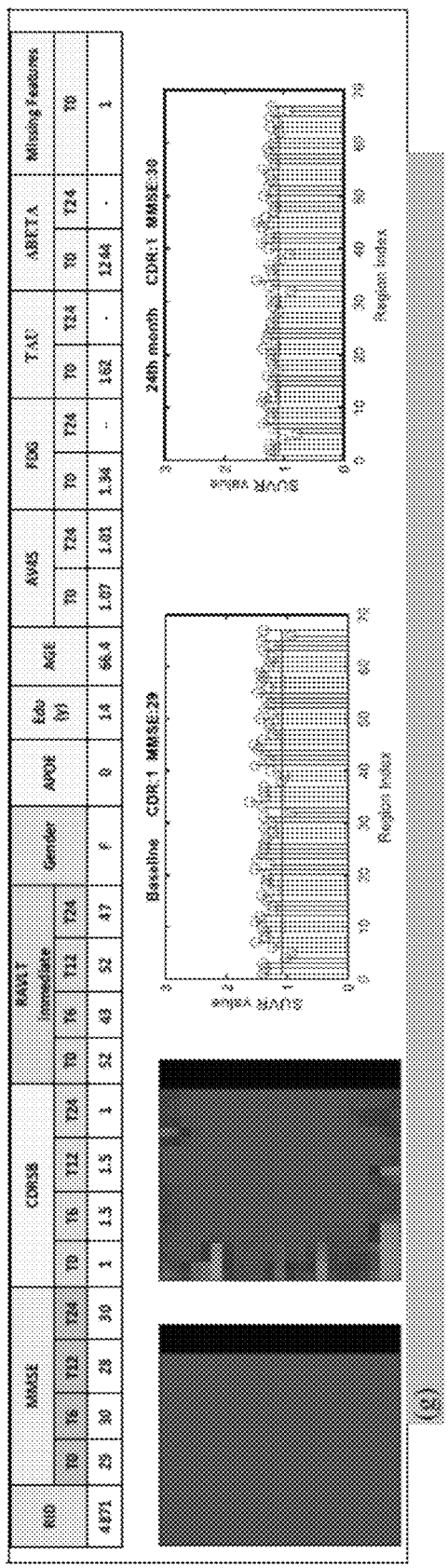
Figure 3H:
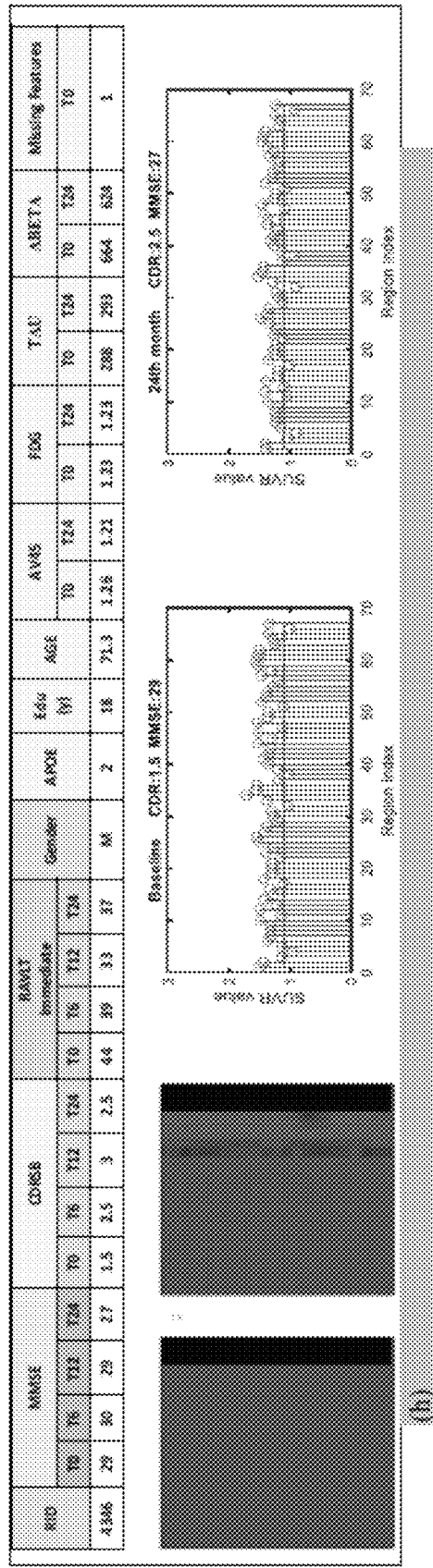
Figure 3I:
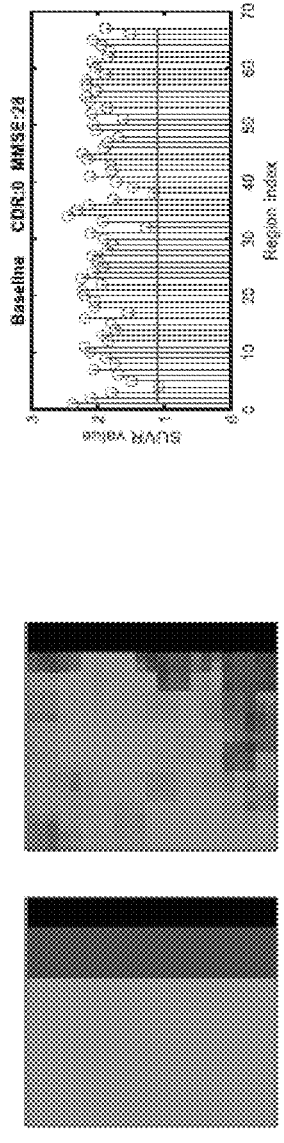
FIGS. 3(i)-3(p) show cases for eight different subjects, respectively, who have transitioned either from CN to MCI or from MCI to AD at different time points.
Figure 3J:
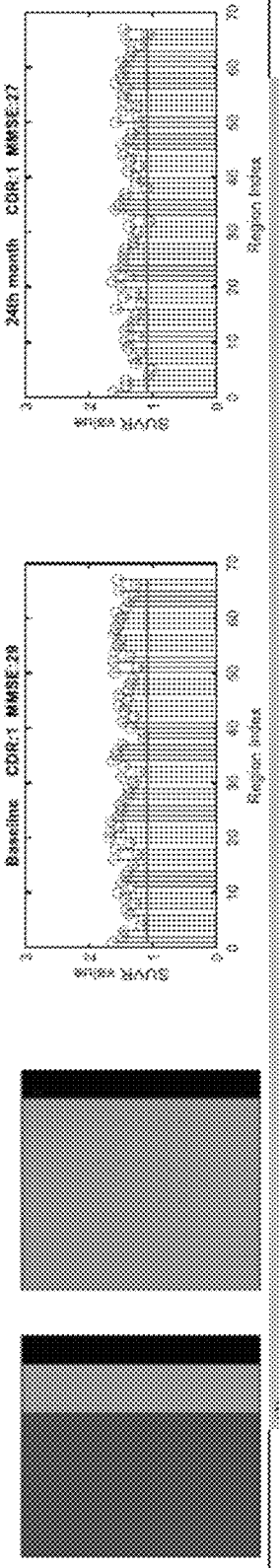
Figure 3K:
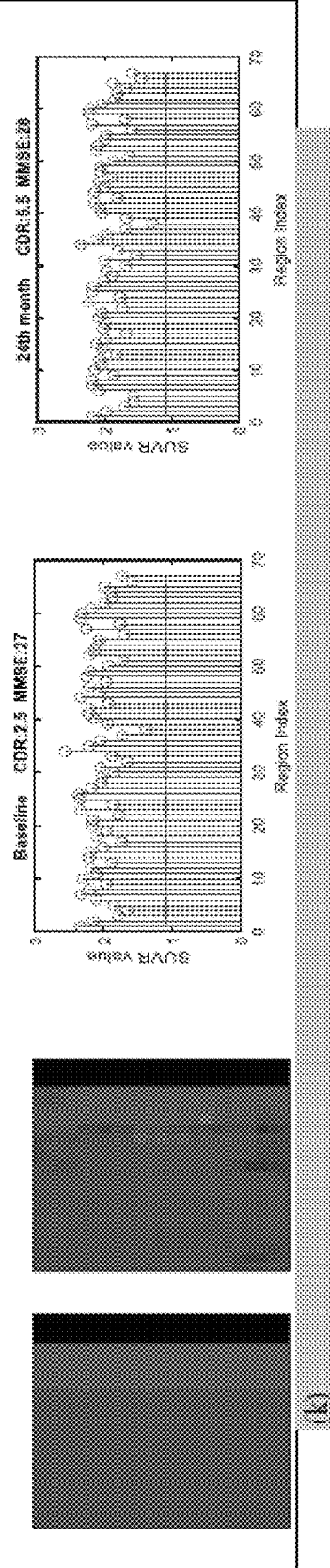
Figure 3L:
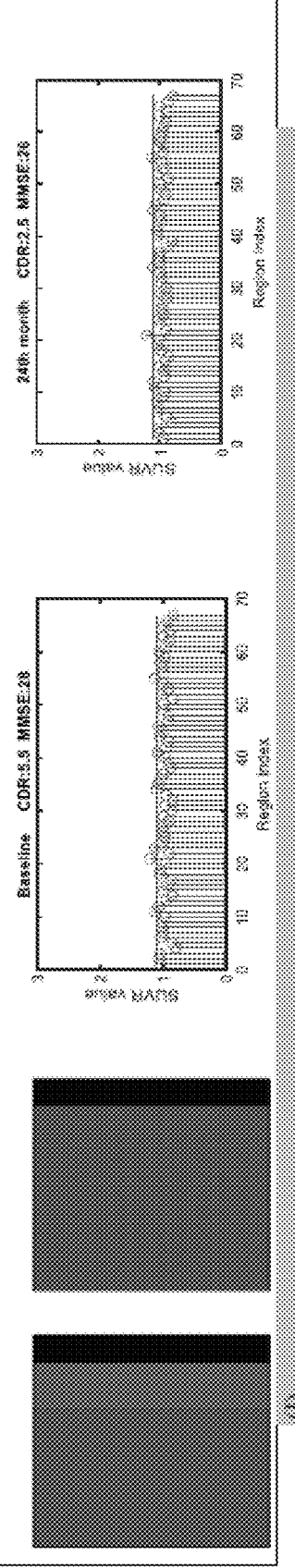
Figure 3M:
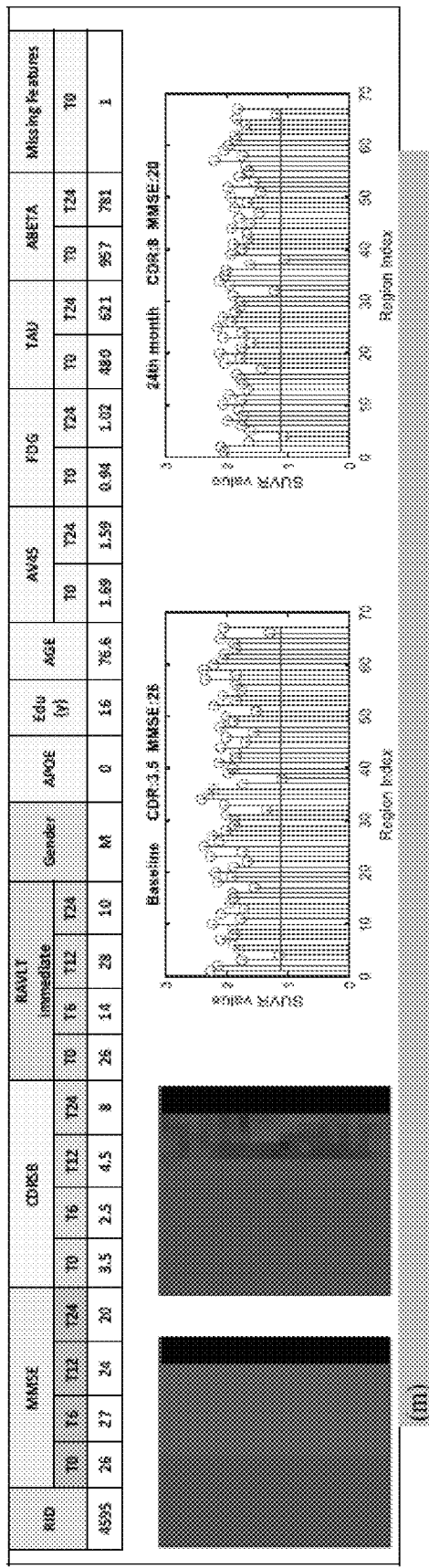
Figure 3N:
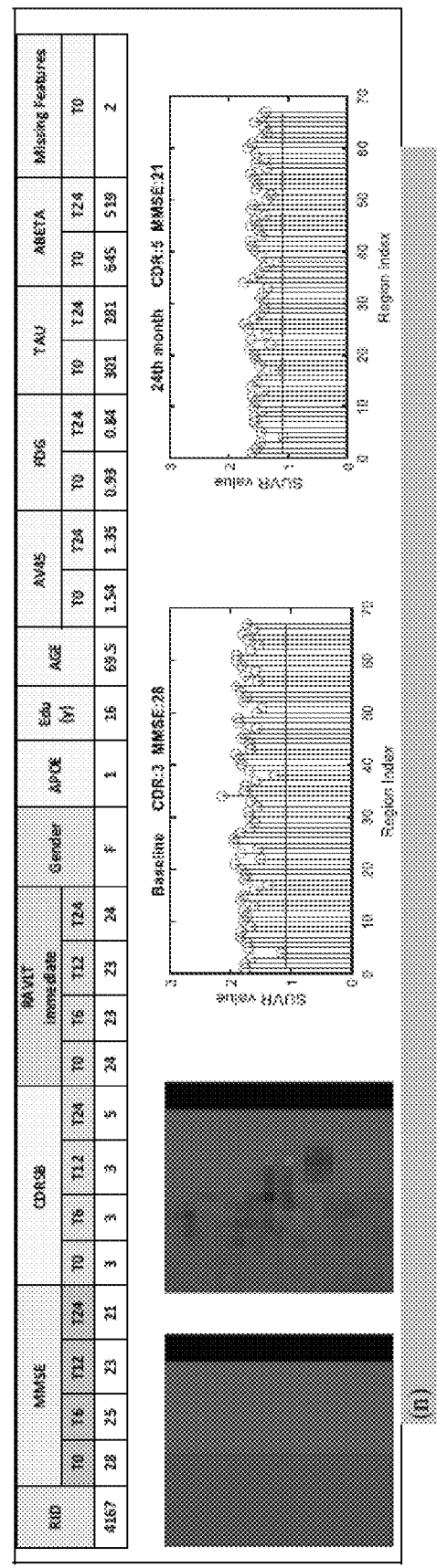
Figure 3O:
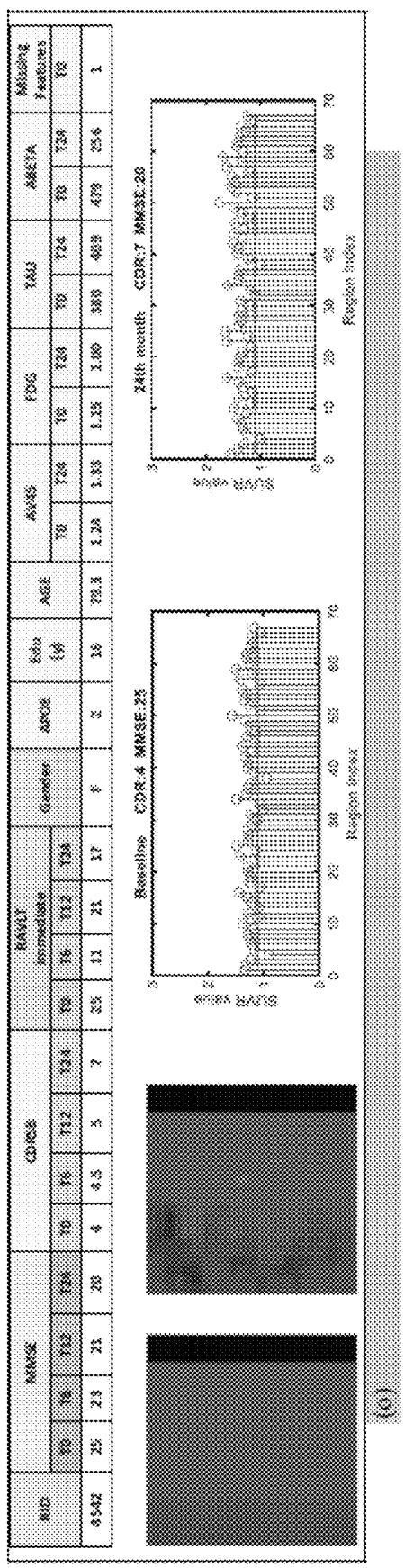
Figure 3P:
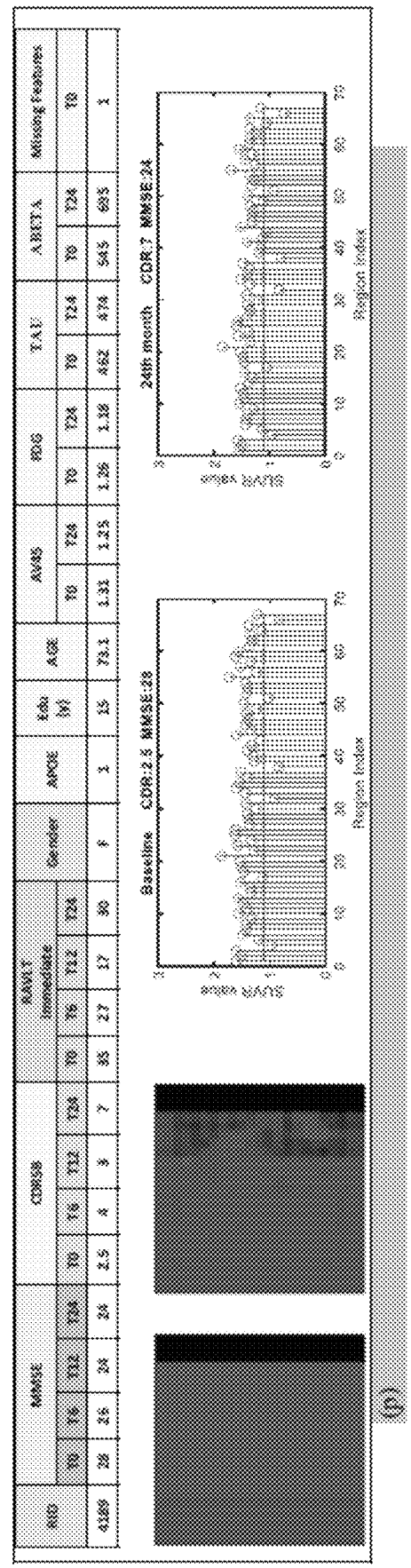
Figures 3Q, 3R:
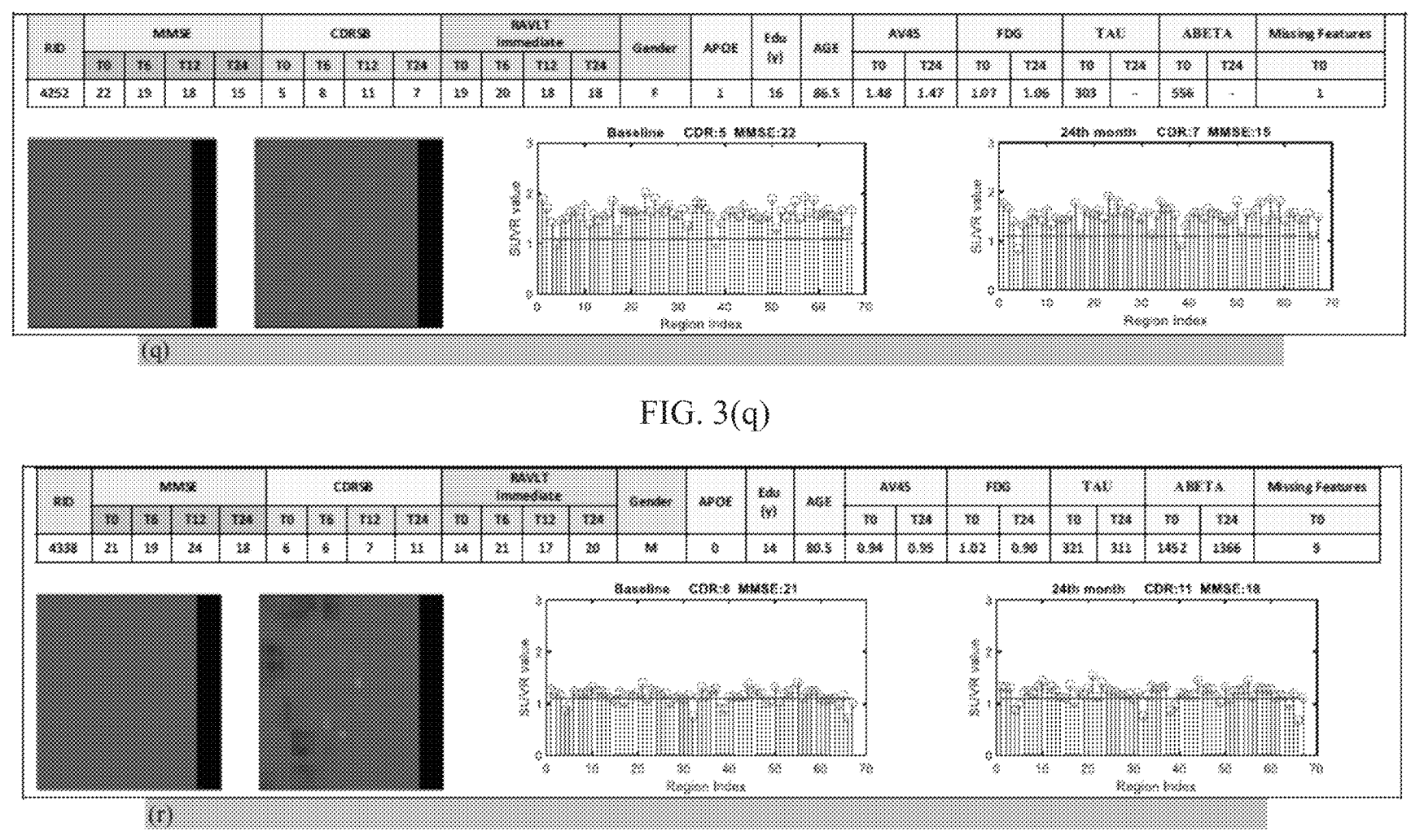
Figure 3S:
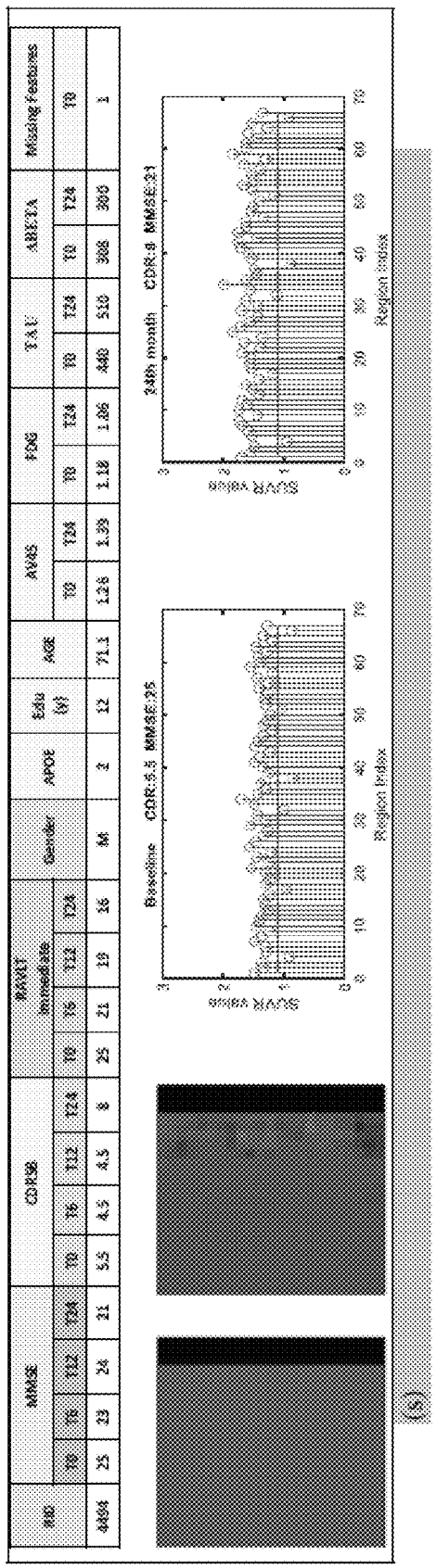
Figure 3T:
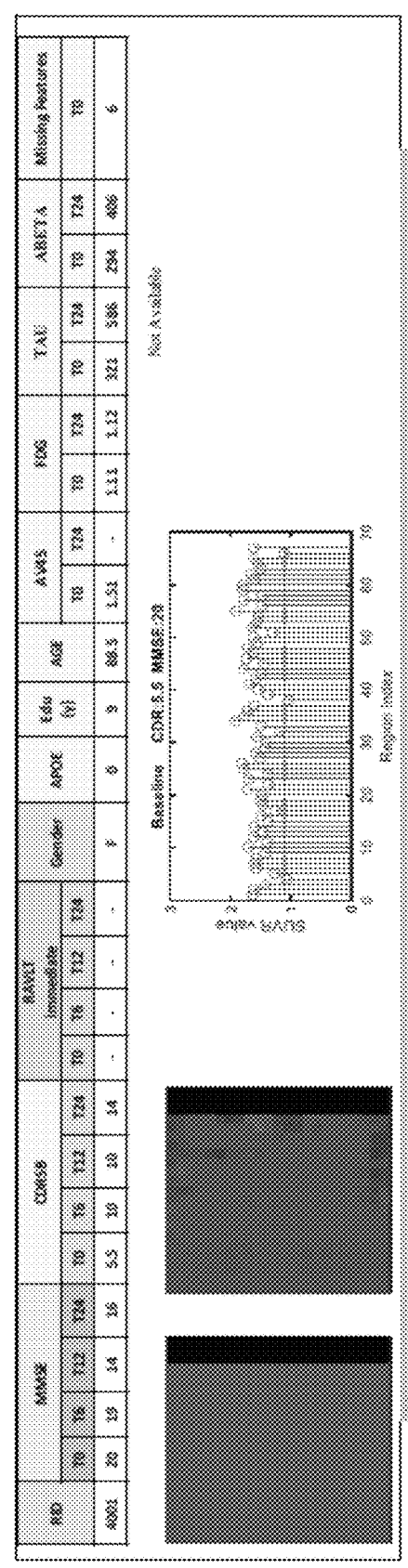
Figure 3U:
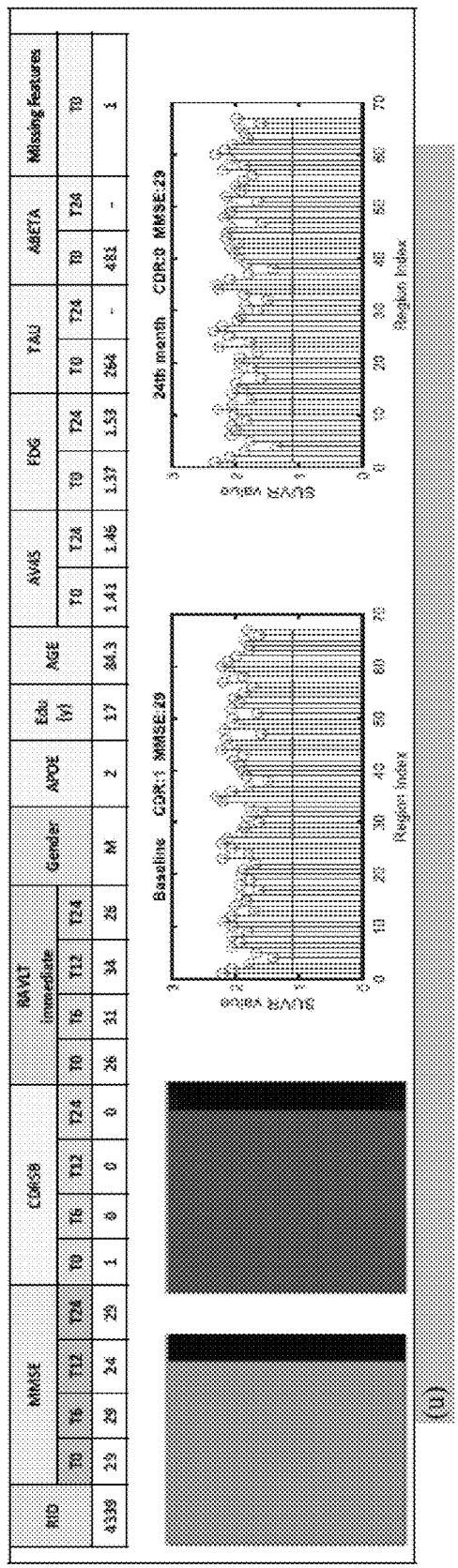
Figures 4A, 4B, 4C, 4D, 4E, 4F, 4G, 4H:
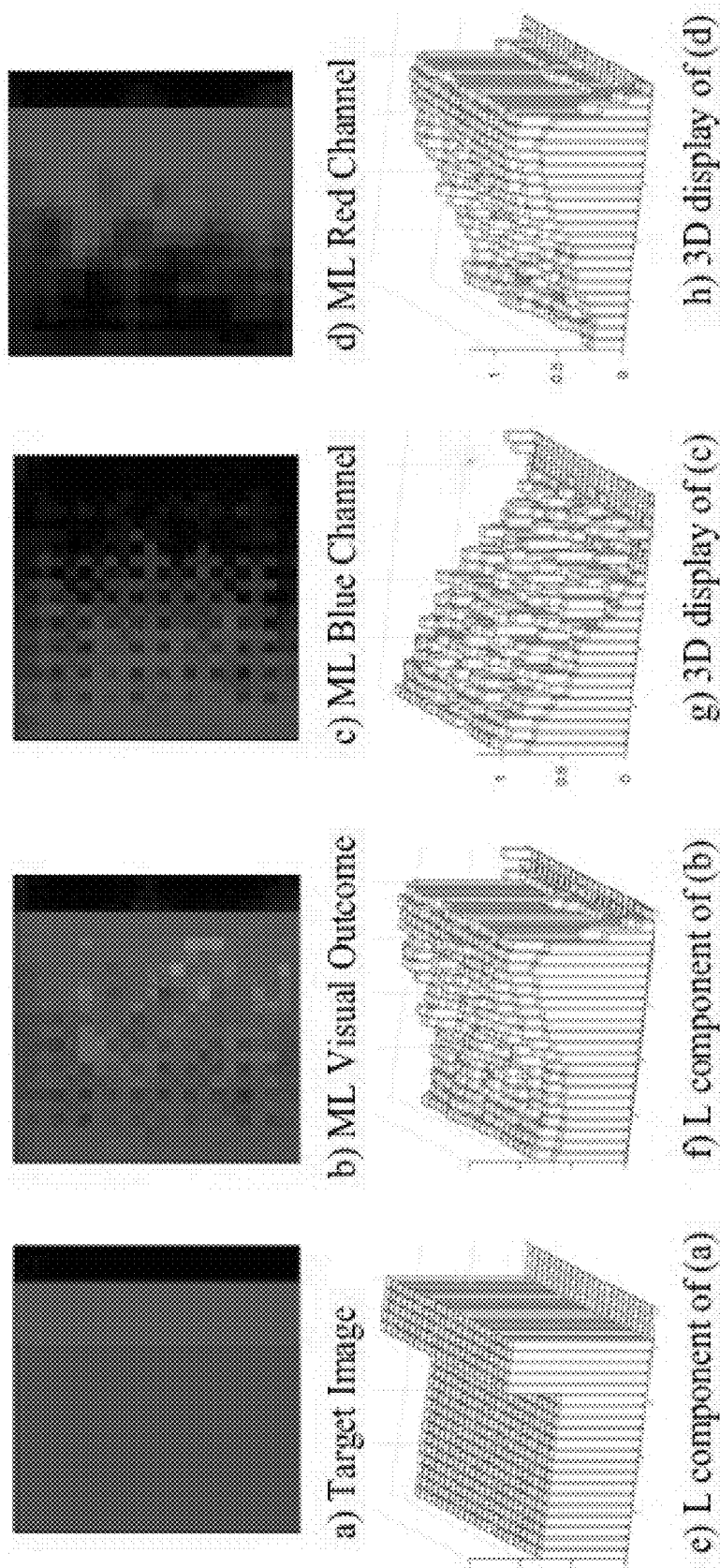
FIGS. 4(a)-4(h) show output images (FIGS. 4(a)-4(d)), L components (FIGS. 4(e) and 4(f)), and three-dimensional (3D) displays (FIGS. 4(g) and 4(h)) for a subject that transitioned from MCI to AD at T24.
Figure 5:
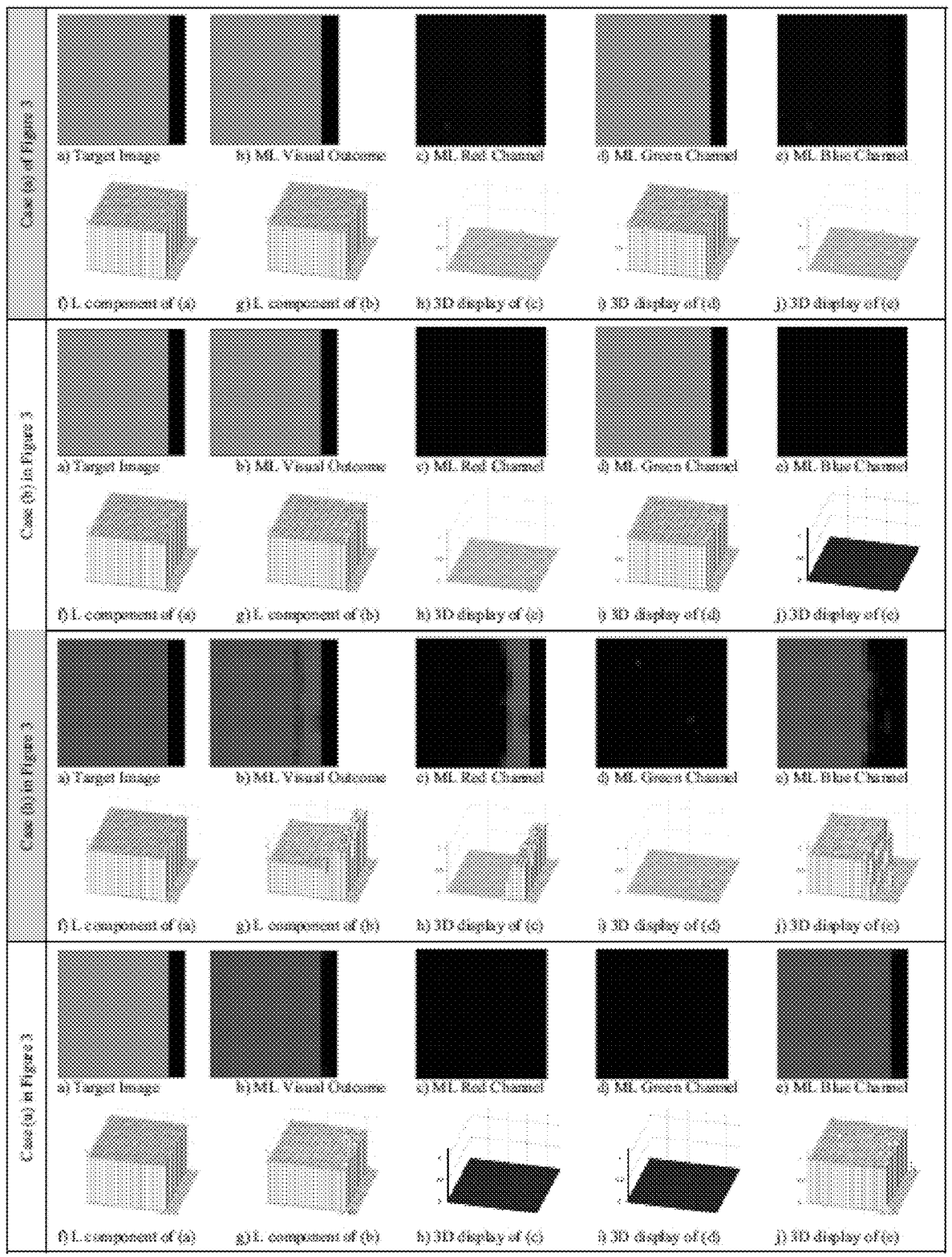
FIG. 5 shows 3D displays of the red-green-blue (RGB) channels for FIG. 3(a) (top section of FIG. 5), 3(b) (second-from-the-top section of FIG. 5), 3(h) (second-from-the-bottom section of FIG. 5), and 3(u) (bottom section of FIG. 5). Within each of the four sections of FIG. 5, across the upper portion is, from left to right, a target image, an ML visual outcome image, an ML red channel image, an ML green channel image, and an ML blue channel image. Within each of the four sections of FIG. 5, across the lower portion is, from left to right, the L component of the target image, the L component of the ML visual outcome image, a 3D display of the ML red channel image, a 3D display of the ML green channel image, and a 3D display of the ML blue channel image.

In many embodiments, the ML model can display the results as a three-dimensional (3D) image as well (see, e.g., FIGS. 4(a)-4(h)). For 3D visualization, the L component of L-a-b format, a 3D variation of the CIE Chromaticity diagram, can be used to display in 3D the RGB format without changing the contextual meaning of the outcomes reflected in the examples considered in FIGS. 4(a)-4(h) and FIG. 5. In this L-a-b format, L refers to lightness normalized from zero to 1, and a and b reflect the colors from green to red for a and from blue to yellow for b. FIGS. 4(a) and 4(b) show the target and ML output images, FIGS. 4(c) and 4(d) illustrate the blue and red channels, respectively, and FIGS. 4(e)-4(h) provide the 3D displays corresponding to FIGS. 4(a)-4(d), respectively. Note the gradual change in the ML-generated visual outcomes. At T24 (24th month), the ML visual outcome in FIG. 4(f) stabilizes at the highest levels near the normalized value of 1. Moreover, as the blue channel reflecting the MCI state declines rapidly between T12 and T24, the red channel in FIG. 4(h) reflecting the AD state increases from T12 through T24 to stabilize at the maximum value of 1. Note how easy it is to ascertain the effect the ML model has on the region of uncertainty in the displays in FIGS. 4(f), 4(g), and 4(h). For the visual appreciation of this 3D display model, four different cases (the cases used for FIGS. 3(a), 3(b), 3(h), and 3(u)) are displayed in FIG. 5.

Visual outcomes of embodiments of the subject invention enhance the processes of multiclass classification and disease projection with the ability to visualize the inner workings of the ML and observe what the differences between the ML visual outcome and target image could mean. In other words, the difference between them does not necessarily mean an outright misclassification but emphasizes the nuances between them and implies that a review may be helpful to investigate what may have led to such change, especially if the RU in the visual display remains unaffected.

It is thus important to recognize that the interrelatedness in features, along with the many variations of such multimodal features, some being temporal, others structural, functional, metabolic, genetic, demographic, or cognitive are extremely difficult to disentangle, especially when combined with subjective thresholds or ranges of scores such as with SUVRs, MMSE, and CDR-SB. When considering ADNI data, there is an overlap in MMSE scores between CN, MCI, and even AD groups, and the CDR-SB values may resolve this overlap. Still, for an ML model, more datasets can help learn more of the interplay between such cognitive features, especially when used for baseline diagnosis.

Embodiments of the subject invention provide new approaches for the visualization-based estimation of disease trajectory to augment the diagnosis and prognosis of AD. A deep learning (DL) architecture, which can be based on one or more convolutional neural networks (CNNs) can generate a visual image that portrays AD trajectory (e.g., in a 2-year longitudinal study) using baseline features only. From the baseline features, in order to avoid bias, all cognitive scores (e.g., MMSE, CDR-SB, and ADAS) can be removed from consideration as input features in certain embodiments. Target images using different colors can define each stage of the disease (e.g., at a plurality of observation time points (such as T0, T6, T12, and/or T24)), with T0 being the baseline time point. A unique characteristic of embodiments of the subject invention is that the model can be trained with known target images with color-coded diagnoses at each time point (e.g., all four time points) to generate a visual output that predicts disease trajectory based on baseline features only. Because only baseline features are used as input, this design is amenable to cross-sectional and longitudinal studies based on similar datasets. This can also lead to new insights as to the gradual changes between transition phases as a function of the input feature space considered.

Embodiments of the subject invention can improve any medical set up, clinic, hospital, or other medical or academic institution involved with AD patients and other health issues related to memory disorders, by providing an enhanced diagnosis and prognosis, along with a determination if any given treatment or therapeutic intervention is having its intended beneficial outcome. Embodiments can be used as a research tool for the research community in academia and medical schools to develop new ML techniques and even attempt to implement algorithms on the ML-visualization design model for potential improvements, for the creation of new visualization models, and to generalize the design concept to other critical health issues.

Embodiments of the subject invention promote in a significant way both science and national health by eliciting a new understanding of a disease that affects 11% of the population over the age of 65 (currently 6.7 million and expected to increase to 12.7 million by 2025, of which 2/3 are women). The growing costs in managing AD are estimated to be $345 billion, according to data reported in the 2023 annual report by the Alzheimer's Association. Hence, all clinics, hospitals, academic institutions, and other associations and organizations can benefit from systems and methods of embodiments of the subject invention, which can be fully accessible onsite or through a remote login.

Embodiments of the subject invention provide a focused technical solution to the focused technical problem of how to assess AD state and/or AD progression in subjects (e.g., human patients). The solution is provided by ML-based color-coded visualization to yield images that express visually disease state and/or progression to augment and facilitate the diagnosis and prognosis of AD. A human agent can also be involved to review the images and make appropriate decisions and/or take appropriate action. The systems and methods of embodiments of the subject invention allow for significantly improved diagnosis and prognosis of AD. Embodiments of the subject invention can improve the computer system performing the ML-based color-coded visualization by outputting only a color-coded image and not a more complex report or series of images (this can free up memory and/or processor usage).

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

Clinical data from the Alzheimer's Disease Neuroimaging Initiative (ADNI) database was used. Only subjects that had a baseline (T0) scan (in at least one modality) and showed up for follow-up visits at T6 (6th month), T12 (12th month), and T24 (24th month) were considered, leading to a total of 1123 subjects as shown in the table in FIG. 6. ADNI categorizes these subjects into the three classes of CN, MCI, and AD at baseline and for each referral session.

The input features used for each modality and the number of observations made at the different time points were obtained from the "QT-PAD Project Data" AD Modelling Challenge (see, www.pi4cs.org/qt-pad-challenge; which is hereby incorporated by reference herein in its entirety), as given in the table shown in FIG. 7. Hence, inputs to the ML model contained features from the baseline, including MRI and PET sequences, demographic information, and specific cognitive measurements. Automatically generated outputs of the ML network were images containing colorful strips expressing disease progression at different time points. It is important to emphasize that in designing the color-coded visualization scheme, and to avoid any bias, the MMSE and the CDR sum of boxes (CDR-SB) scores were excluded from the input feature space in the training and testing phases because both are used for the labeling of subjects. Further, the Alzheimer's Disease Assessment Scores (ADAS11, ADAS13) were also removed from consideration as they correlate well with MMSE and CDR-SB. Each feature f of the input feature vector, e.g. FDG, was normalized by mean normalization over all its non-missing values (set F); i.e., $f\_normalized = (f - mean(F))/(max(F) - min(F))$.

After normalization, it was ensured that the missing values do not affect network training. The QT dataset implicitly reports values of some features as ABETA>1700, for example. For this reason, during preprocessing of the data, ABETA of those samples higher than 1700 or smaller than 200 were replaced by 1700 and 200, respectively. Similarly, PTAU values greater than 120 and smaller than 8 were replaced by 120 and 8, respectively. Also, TAU values greater than 1300 and less than 80 were replaced by 1300 and 80, respectively.

The loss function was the MAE between the target image and the produced output (i.e., loss=MAE($I_{target}-I_{predicted}$)) as defined above. The 10-fold cross-validation over subjects was used, and in each training session, 10% of the training set was used as a validation set (i.e., ten times of training data split to 81/9/10% as train/validation/test). 4000 epochs were used with a batch size of 500 to train the network. In order to produce a larger 45×45 image size, the L8 layer was replicated (in comparison to the architecture shown in FIG. 2). The network made use of the Keras TensorFlow deep learning frameworks. Using the GPU NVIDIA Geforce RTX 2080, the table shown in FIG. 8 provides the processing time it took from feeding the input to the ML model to obtaining the visual outcome as a function of the image size.

Example 1

Figure 3V:
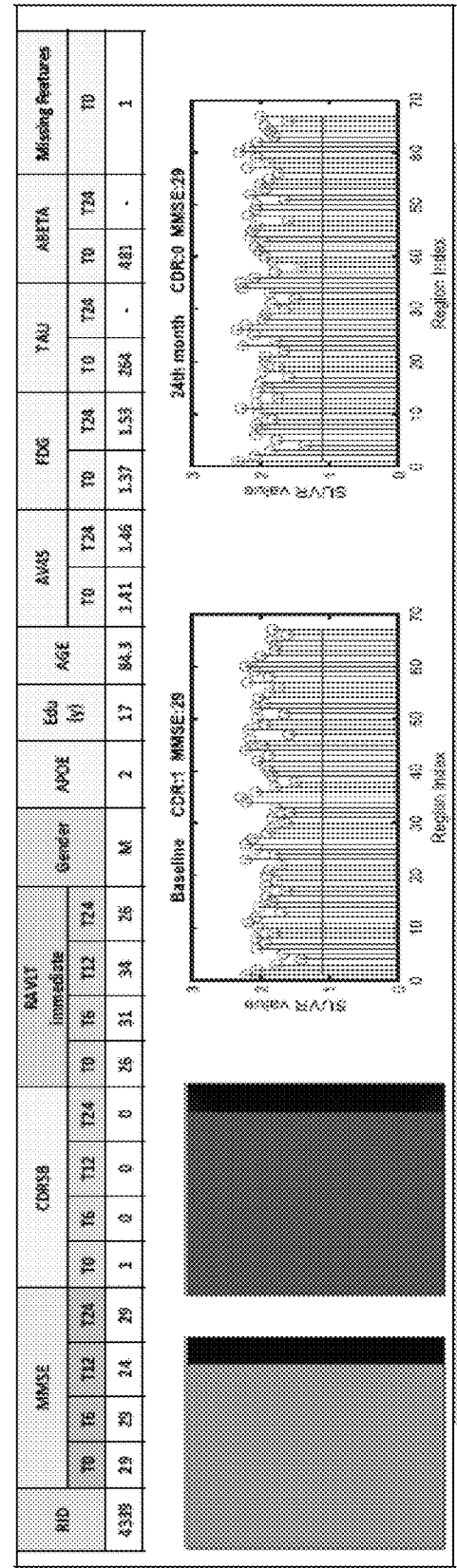
Figure 3W:
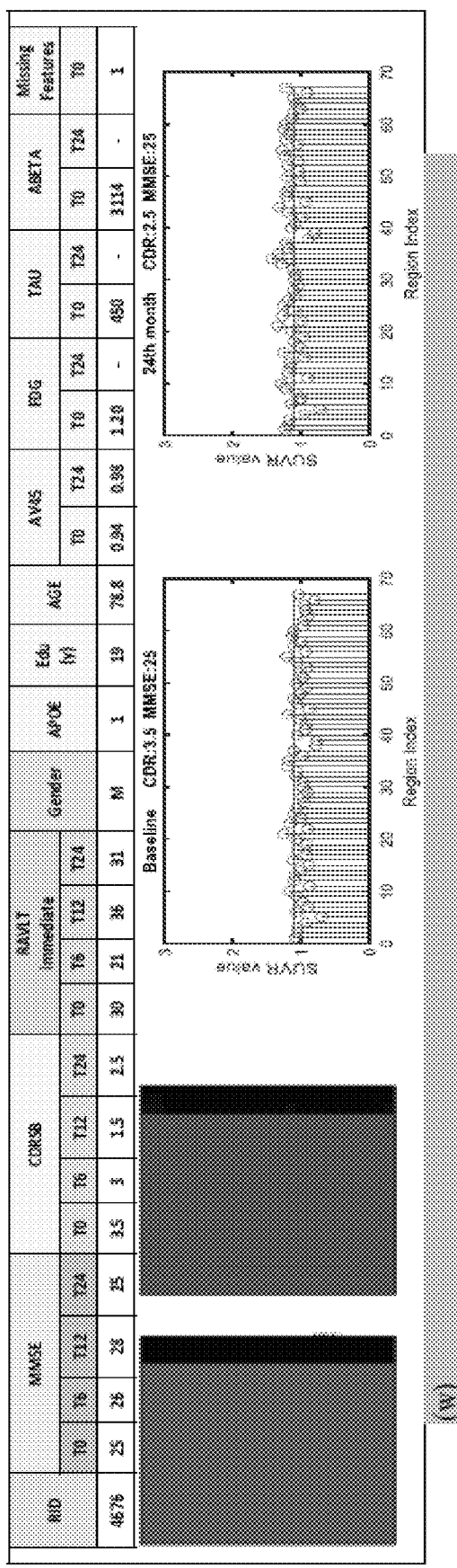

In order to demonstrate the merits of the visualization platform, different scenarios were considered, as shown in FIGS. 3(a)-3(w), including stable subjects over time and subjects that transition from one state to another at different time points. These varied examples highlight the practical merits the color-coded visualization of embodiments of the subject invention has in facilitating diagnosis and prognosis of AD. For each subject in the testing phase (not seen in the training phase), color-coded patterns were generated based solely on observed features at baseline.

FIGS. 3(a)-3(w) provide several examples that reflect different target images and the respective visual outputs that the ML model produced in the test phase. In each image pair located in the lower left portion of each of FIGS. 3(a)-3(w), the target image is on the left (of the image pair) and the ML visual output is on the right (of each image pair). In order to include different scenarios for all the 1123 subjects considered, four cases are shown for each of the stable CN group with the green-colored target at all four-time points (FIGS. 3(a)-3(d)), stable MCI with a blue-colored target (FIGS. 3(e)-3(h)), eight different transition cases that include examples of subjects who transitioned from CN to MCI or from MCI to AD with one case from MCI to CN at different time points (FIGS. 3(i)-3(p)), and four examples of stable AD subjects (FIGS. 3(q)-3(t)). FIGS. 3(u)-3(w) show three selected cases (all stable cases) where the ML model misclassified as belonging to a different stable disease state.

For a more meaningful assessment of disease trajectory, as all these different cases were considered, context is provided in FIGS. 3(a)-3(w) for augmented interpretability of the challenging cases. For this added context, MMSE, CDR-SB, and RAVLT scores are provided for all four time points (T0, T6, T12, and T24), as well as age, sex, years of education, the APOE, AV45, FDG, TAU, ABETA, number of missing features at baseline, and graphs of the SUVR measurements at T0 (baseline) and T24 (24th month), where the x-axis reflects the different brain regions for the SUVRs as annotated in the table shown in FIG. 10. The scores/values used for MMSE and CDR-SB conform to the standards defined by ADNI. The APOE value of 0, 1, or 2 specifies a carrier of zero, one, or two APOE e4 alleles. For all these displayed cases, the intent was to use such context to deliberate on what may have led to the differences between target images and the ML visual outcomes.

It can be observed that most stable cases were classified correctly and that the misclassified cases often were those that experienced a transition phase of the disease. The cases for FIGS. 3(a), 3(b), 3(k), 3(n), and 3(q) clearly show that the ML visual outcome agrees with the target image. Even in cases like those for FIGS. 3(c), 3(e), 3(o), and 3(r), although the ML outcome is slightly different from the target, they are still mostly similar, and the three raters (see Example 3) had no problem classifying them correctly. However, for the three cases for FIGS. 3(u), 3(v), and 3(w), although the changes were minor, this could still lead to a misclassification with a strict rater or when relying solely on ML without the benefit of visual output. Through many nuanced visual versions of the ML model in contrast to the target image, the difficulties typically faced in reaching high classification results can be appreciated, especially in multiclass classification and longitudinal studies.

Referring again to FIGS. 3(a)-3(w), although the neuropsychological test scores MMSE, CDR-SB, and ADAS were excluded from the training and testing phases of the ML model, these cognitive scores still show significant consistency with the outcome of the ML. For example, in the case for FIG. 3(c), the stable CN is shown to transition to MCI in T12 and T24 just as the CDRSB scores changed from 0 to 0.5, which indicates questionable impairment in the staging cate-gory, even when the MMSE score is stable at 30, which is the maximum score one can get. The case for FIG. 3(h) is another interesting outcome of the ML model, as it shows a transition to AD in T24 due perhaps to the change of the CDR-SB score to 3 and 2.5, respectively, with a score of 3 indicating very mild dementia in the staging category. Note also for this case that the MMSE dropped from 30 to 27, with mild AD defined in the 21-26 range. A case that is hard to explain is the case for FIG. 3(j), which can be defined as "other" in the classification categories. In this case, it seems that the MCI patient reverted to CN at T24, yet the ML model determined that this is a case of a stable CN. In such cases, where the MMSE scores, as well as the CDR-SB, are ambiguous from the diagnosis standpoint at baseline, such cases should be reviewed in context to all other inputs to the ML model to look into the neuroimaging data and other cognitive scores to determine what led to this transition in the diagnosis at baseline. The case for FIG. 3(i) is also interesting, where a stable CDR-SB of 0 scores (which means no impairment) and high MMSE scores from 28 to 30, the ML model is attempting to render visually a stable CN instead of the clear transition to MCI seen in the target image. The more complex cases for FIGS. 3(m) and 3(p) may reveal that the ML model didn't do as well when the MMSE scores and CDR-SB scores vary in ways that are difficult to decipher from one phase in time to another with the target image reflecting the diagnosis at baseline may be the correct one. The cases for FIGS. 3(s) and 3(t) are misclassified, especially given the low MMSE scores and the high CDR-SB scores; however, the high number of missing values for the case for FIG. 3(t) should be noted. Even with these examples discussed, the merits of the visualization process is demonstrated, where these types of contextual deliberations would not otherwise be possible if the ML classification algorithm was relied on solely without recourse to a visualized output.

By having recourse to a visual outcome, challenging cases can be reassessed to determine what could have led to such an ML outcome and whether there is more reason to assert a misclassification or instead accept the ML outcome as the more appropriate diagnosis.

Overall, the results compared favorably to related art systems and methods.

In addition, the results of the implementation of ML4VisAD showed the need for deep reflection when assessing multiclass classification or prediction results using ML, especially when observing all the subtle nuances of the visual outcome. There were a few cases where the ML4VisAD visual output seemed to make more sense than what the target images portrayed, especially concerning the available measurements at the different time points. The case for FIG. 3(j) shows a subject that transitioned back to normal control (CN) from an MCI diagnosis in the previous three time points. The ML model did not see it the same way and had the subject as stable CN through all four time points, and most measurements support this classification. Another example is the case for FIG. 3(l), where the target showed a transition from MCI to AD in T24, while the ML4VisAD visual output displayed a stable MCI through all time points. Here again, the measurements are somewhat ambiguous but more in favor of the ML model in that the MMSE did drop but only by one point in T24 compared to T6, and the CDR-SB scores are otherwise consistent through T6 to T24 with the SUVR also consistent in T0 and T24. Another interesting case was that for FIG. 3(v), where the target image shows a stable MCI, while the ML4VisAD visual output places this subject as stable CN. In this case, from the high MMSE score, the low SUVR values, and an APOE of 0, although the CDR is 0.5, the ML visual outcome of a stable CN seems more reasonable. Other cognitive tests (ADAS, RAVLT) may have influenced the diagnosis, and these scores were not used in the ML4VisAD model to avoid bias. In many of these cases, consideration could be given to generating a composite score (see also, e.g., Jelistratova et al, Longitudinal validity of PET-based staging of regional amyloid deposition, Hum Brain Mapp 2020, doi.org/10.1002/hbm.25121; which is hereby incorporated by reference herein in its entirety). For the cases for FIGS. 3(u), 3(v), and 3(w), all stable cases misclassified as another type of stable cases, and there seems to be an influence of the APOE value on the ML4VisAD outcome (0 influences the CN state, 2 switched CN to MCI, and 1 reverted AD to MCI).

These ML visual outcomes clearly show why clinicians face difficulty each time they deliberate on a patient's disease state. For example, it is hard to understand why the subject in the case for FIG. 3(u) had an MMSE score of 29 for T0, T12, and T24 but an MMSE score of 24 at time T6. Also, for the same patient the CDR score was 1 at T0 and reverted to 0 for all subsequent time points. Although the diagnosis is that of a stable CN for this case, the ML visual outcome placed this subject as stable MCI when considering all other features. Recall that the APOE for the case for FIG. 3(u) is 2 at baseline and that the SUVRs are relatively high. Also, the high number of years of education for this subject (17) may have led to the high MMSE scores of 29 for T0, T12, and T24, although stumbling in the test given at T6.

The subtle nuances encountered with the ML4VisAD visual outcomes can reduce misclassifications with added scrutiny on the visual output in context to specific measurements clinicians may be interested in. Consequently, the first point is that multiclass classification, whether it is automated or made through a rating process, does not allow for a more thorough deliberation process if these nuances and subtle differences cannot be visually observed and would be so hard to decipher otherwise through tabulated data or decisional spaces showing different overlapped regions among the considered classes. Therefore, the more classes considered in a multiclass classification algorithm, the less accurate will the classification results be. In addition, the visualization provided by embodiments of the subject invention can greatly improve on this process.

Example 2

In order to acquire feedback from the research community on the practicality of this visualization platform, an online survey was conducted using the Qualtrics platform and shared via Facebook® and LinkedIn®. More than 100 persons participated in this survey globally, confirming the importance of embodiments of the subject invention in ease of use and in facilitating the decision-making process. This survey showed that 83.49% of participants agree that the visual representation is easy to remember and interpret, with 79.55% stating that they would prefer to receive the results in a graphic format. An overwhelmingly favorable rating of 82.35% was received in terms of ease of memorizing/remembering the output through visualization, with 73.79% agreeing that the visualized form speeds up the decision-making process. As for the level of uncertainty (i.e., trustfulness of the output), 81.65% stated that different levels of trustfulness are visible in the visualized format.

Example 3

Separate from the survey results in Example 3, three raters (identified as M.E., S.T., and M.S.) independently reviewed all ML-generated visual outcomes for both types of classification: 3-way (CN, impaired, others) and 5-way (CN, MCI, MCIc, AD, others) using a developed MATLAB-based user interface (demo: youtube/yQWFo33RYiQ). Each rater was to view each ML visual output and classify it. "Others" included those that converted back to CN from MCI or to MCI from AD. The results in the table shown in FIG. 9 show that when using a 3-way classification, the ML model was relatively accurate with an 82% (±3%) accuracy, and for a 5-way classification, the accuracy dropped to 68% (±5%). The achieved accuracy is consistent with the state of the art.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for color-coded visualization to aid in diagnosis and prognosis of Alzheimer's disease (AD), the system comprising:
   a processor; and
   a machine-readable medium in operable communication with the processor and having instructions stored thereon that, when executed by the processor, perform the following steps:
   a) receiving multimodal input data about a subject, the multimodal input data comprising neuroimaging data of the subject;
   b) utilizing a machine learning (ML) model on the multimodal input data to perform intra-modality feature extraction and inter-modality feature extraction, followed by multimodal fusion to give fused data; and
   c) utilizing the ML model to perform tensorization on the fused data to generate a visual output image, the visual output image being color-coded based on a prognosis of AD for the subject,
   the ML model comprising:
   a first part comprising a first plurality of layers configured to perform the intra-modality feature extraction, the inter-modality feature extraction, and the multimodal fusion; and a second part comprising a second plurality of layers configured to perform the tensorization on the fused data to generate the visual output image.

2. The system according to claim 1, the neuroimaging data comprising magnetic resonance imaging (MRI) data of the subject and positron emission tomography (PET) of the subject.

3. The system according to claim 1, the multimodal input data further comprising cerebrospinal fluid (CSF) biomarker data of the subject, cognitive task result data of the subject, and risk factor data of the subject.

4. The system according to claim 1, the second part being further configured to perform extra feature extraction on the fused data.

5. The system according to claim 1, the second part being further configured to perform drop-out and batch normalization on the fused data.

6. The system according to claim 1, the first plurality of layers comprising at least five layers, and
the second plurality of layers comprising at least five layers.

7. The system according to claim 1, the visual output image being color-coded such that:
a first color represents cognitively normal (CN);
a second color different from the first color represents mild cognitive impairment (MCI); and
a third color different from the first color and the second color represents AD.

8. The system according to claim 7, the visual output image comprising a bar representing a region of uncertainty (RU), the bar being a fourth color that is different from the first color, the second color, and the third color.

9. The system according to claim 8, the visual output image being color-coded such that:
a fifth color different from the first color, the second color, the third color, and the fourth color represents early MCI (EMCI); and
a sixth color different from the first color, the second color, the third color, the fourth color, and the fifth color represents late MCI (LMCI).

10. A method for color-coded visualization to aid in diagnosis and prognosis of Alzheimer's disease (AD), the method comprising:
a) receiving multimodal input data about a subject, the multimodal input data comprising neuroimaging data of the subject;
b) utilizing a machine learning (ML) model on the multimodal input data to perform intra-modality feature extraction and inter-modality feature extraction, followed by multimodal fusion to give fused data; and
c) utilizing the ML model to perform tensorization on the fused data to generate a visual output image, the visual output image being color-coded based on a prognosis of AD for the subject,
the ML model comprising:
a first pan comprising a first plurality of layers configured to perform the intra-modality feature extraction, the inter-modality feature extraction, and the multimodal fusion; and
a second art comprising a second plurality of lavers configured to perform the tensorization on the fused data to generate the visual output image.

11. The method according to claim 10, the neuroimaging data comprising magnetic resonance imaging (MRI) data of the subject and positron emission tomography (PET) of the subject.

12. The method according to claim 10, the multimodal input data further comprising cerebrospinal fluid (CSF) biomarker data of the subject, cognitive task result data of the subject, and risk factor data of the subject.

13. The method according to claim 10, the second part being further configured to perform extra feature extraction on the fused data and drop-out and batch normalization on the fused data.

14. The method according to claim 10, the first plurality of layers comprising at least five layers, and
the second plurality of layers comprising at least five layers.

15. The method according to claim 10, the visual output image being color-coded such that:
a first color represents cognitively normal (CN);
a second color different from the first color represents mild cognitive impairment (MCI);
a third color different from the first color and the second color represents AD; and
the visual output image comprises a bar representing a region of uncertainty (RU), the bar being a fourth color that is different from the first color, the second color, and the third color.

16. The method according to claim 15, the visual output image being color-coded such that:
a fifth color different from the first color, the second color, the third color, and the fourth color represents early MCI (EMCI); and
a sixth color different from the first color, the second color, the third color, the fourth color, and the fifth color represents late MCI (LMCI).

17. A system for color-coded visualization to aid in diagnosis and prognosis of Alzheimer's disease (AD), the system comprising:
a processor; and
a machine-readable medium in operable communication with the processor and having instructions stored thereon that, when executed by the processor, perform the following steps:
a) receiving multimodal input data about a subject;
b) utilizing a machine learning (ML) model on the multimodal input data to perform intra-modality feature extraction and inter-modality feature extraction, followed by multimodal fusion to give fused data; and
c) utilizing the ML model to perform tensorization, extra feature extraction, and drop-out and batch normalization on the fused data to generate a visual output image, the visual output image being color-coded based on a prognosis of AD for the subject,
the multimodal input data comprising magnetic resonance imaging (MRI) data of the subject, positron emission tomography (PET) of the subject, cerebrospinal fluid (CSF) biomarker data of the subject, cognitive task result data of the subject, and risk factor data of the subject,
the ML model comprising:
a first part comprising a first plurality of layers configured to perform the intra-modality feature extraction, the inter-modality feature extraction, and the multimodal fusion; and
a second part comprising a second plurality of layers configured to perform the tensorization, the extra feature extraction, and the drop-out and batch normalization on the fused data to generate the visual output image, the first plurality of layers comprising at least five layers,
the second plurality of layers comprising at least five layers, and
the visual output image being color-coded such that:
- a first color represents cognitively normal (CN);
- a second color different from the first color represents mild cognitive impairment (MCI); and
- a third color different from the first color and the second color represents AD; and
- the visual output image comprises a bar representing a region of uncertainty (RU), the bar being a fourth color that is different from the first color, the second color, and the third color.

18. The system according to claim 17, the visual output image being color-coded such that:
- a fifth color different from the first color, the second color, the third color, and the fourth color represents early MCI (EMCI); and
- a sixth color different from the first color, the second color, the third color, the fourth color, and the fifth color represents late MCI (LMCI).

\* \* \* \* \*